US010493455B2

(12) United States Patent
Haggins, Jr. et al.

(10) Patent No.: US 10,493,455 B2
(45) Date of Patent: Dec. 3, 2019

(54) DEVICE AND METHOD FOR ISOLATION OF CORNEAL ENDOTHELIAL CELLS

(71) Applicant: THE UNITED STATES OF AMERICA AS REPRESENTED BY THE SECRETARY OF THE ARMY, Fort Detrick, MD (US)

(72) Inventors: Robert Haggins, Jr., Belcamp, MD (US); Erik Eaton, Jr., Havre de Grace, MD (US); Zachary Murray, Jarrettsville, MD (US); Timothy Varney, Baltimore, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 16/171,797

(22) Filed: Oct. 26, 2018

(65) Prior Publication Data
US 2019/0060903 A1 Feb. 28, 2019

Related U.S. Application Data

(63) Continuation-in-part of application No. 16/060,078, filed as application No. PCT/US2017/028242 on Apr. 19, 2017, now Pat. No. 10,443,032.
(Continued)

(51) Int. Cl.
C12M 3/00 (2006.01)
C12M 1/00 (2006.01)
(Continued)

(52) U.S. Cl.
CPC ... B01L 3/502761 (2013.01); B01L 3/502769 (2013.01); C12N 5/0621 (2013.01);
(Continued)

(58) Field of Classification Search
CPC ...... C12M 29/10; C12M 29/06; C12M 21/08; C12M 23/10; C12M 25/06
See application file for complete search history.

(56) References Cited

U.S. PATENT DOCUMENTS 3,745,091 A    7/1973  McCormick
6,670,170 B1 * 12/2003  Gaffin .................... C12M 23/10
                                                  435/288.3
(Continued)

FOREIGN PATENT DOCUMENTS

DE   102014222547 B3    2/2016
EP         280610 A1   11/2014

OTHER PUBLICATIONS

Thiel et al.: "A simple corneal perfusion chamber for drug penetration and toxicity studies", British Journal of Ophthamology, vol. 85, No. 4, Apr. 1, 2001 (Apr. 1, 2001), pp. 450-453, XP002772567, figures 1,2.

Primary Examiner — Nathan A Bowers
(74) Attorney, Agent, or Firm — Leigh Callander; William Eshelman

(57) ABSTRACT

An apparatus for isolating corneal endothelial cells (CECs) includes a housing with an interior wall that defines a hollow interior of the housing. At least four fluid channels are formed in the housing with two of the channels terminating in respective openings in an upper portion of the interior wall and two of the channels terminating in respective jets in the upper portion of the interior wall. A convex projection is centrally located on the circular base of the hollow interior and is configured to receive an inverted cornea. A circular insert for the housing has an opening therein in which the convex projection projects when the insert is mated with the lower portion of the interior wall. CECs are harvested from the inverted cornea.

20 Claims, 20 Drawing Sheets

Related U.S. Application Data

(60) Provisional application No. 62/324,476, filed on Apr. 19, 2016.

(51) Int. Cl.
*B01L 3/00* (2006.01)
*C12N 5/079* (2010.01)

(52) U.S. Cl.
CPC .................. *B01L 2200/0652* (2013.01); *B01L 2300/0877* (2013.01); *B01L 2300/14* (2013.01)

(56) References Cited

U.S. PATENT DOCUMENTS

| | | |
|---|---|---|
| 7,169,578 B2 | 1/2007 | Wang et al. |
| 7,371,584 B2 | 5/2008 | Feistel |
| 7,799,520 B2 | 9/2010 | Ross et al. |
| 8,309,344 B2 | 11/2012 | Chang et al. |
| 8,609,408 B2 | 12/2013 | Fan et al. |
| 2006/0025577 A1 | 2/2006 | Ferrara et al. |
| 2014/0170751 A1 | 6/2014 | Hayashi et al. |
| 2014/0357511 A1 | 12/2014 | Handique et al. |
| 2015/0168278 A1 | 6/2015 | Hale |
| 2016/0008408 A1 | 1/2016 | Imagawa et al. |
| 2016/0029618 A1 | 2/2016 | Gain et al. |
| 2019/0002818 A1* | 1/2019 | Haggins, Jr. ............ C12M 47/04 |
| 2019/0094208 A1* | 3/2019 | Vuong ............... G01N 33/5085 |

* cited by examiner

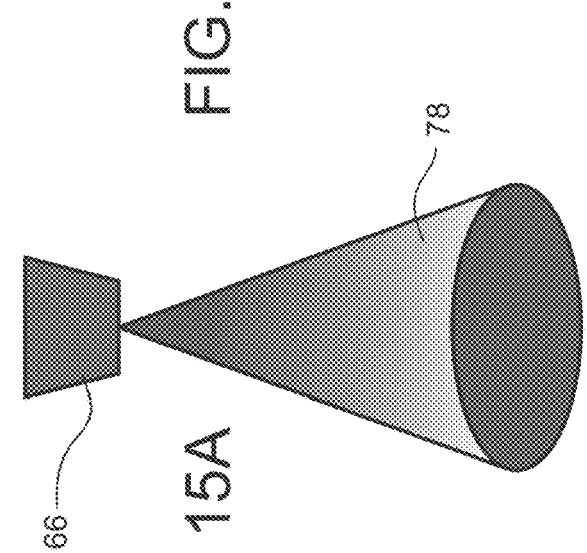
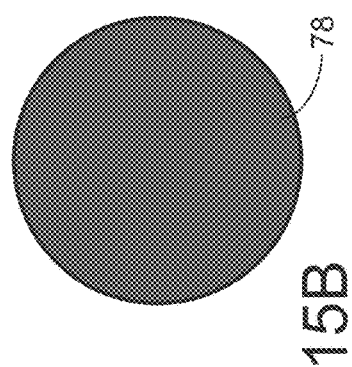
FIG. 15A  FIG. 15B
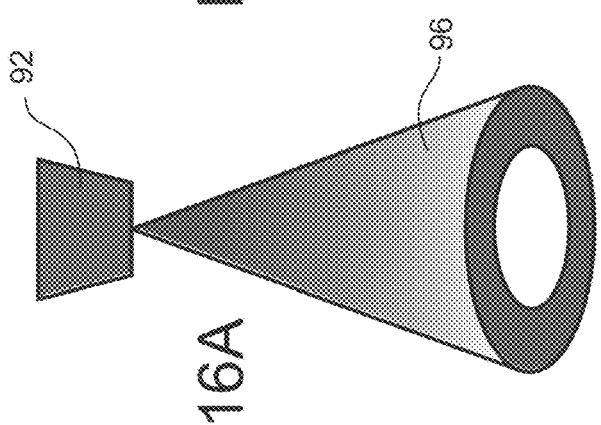
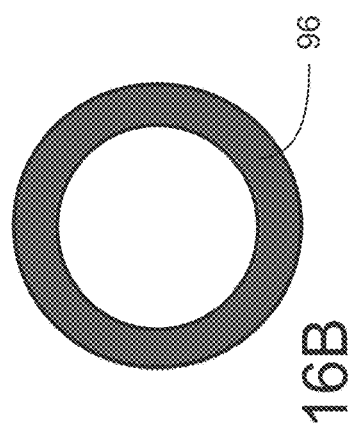
FIG. 16A  FIG. 16B
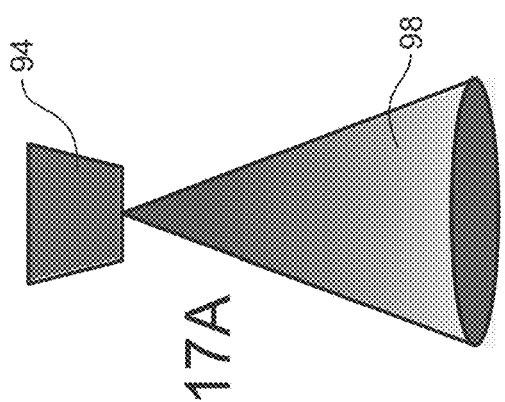
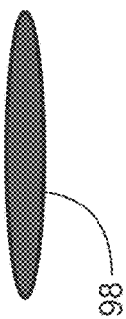
FIG. 17A  FIG. 17B

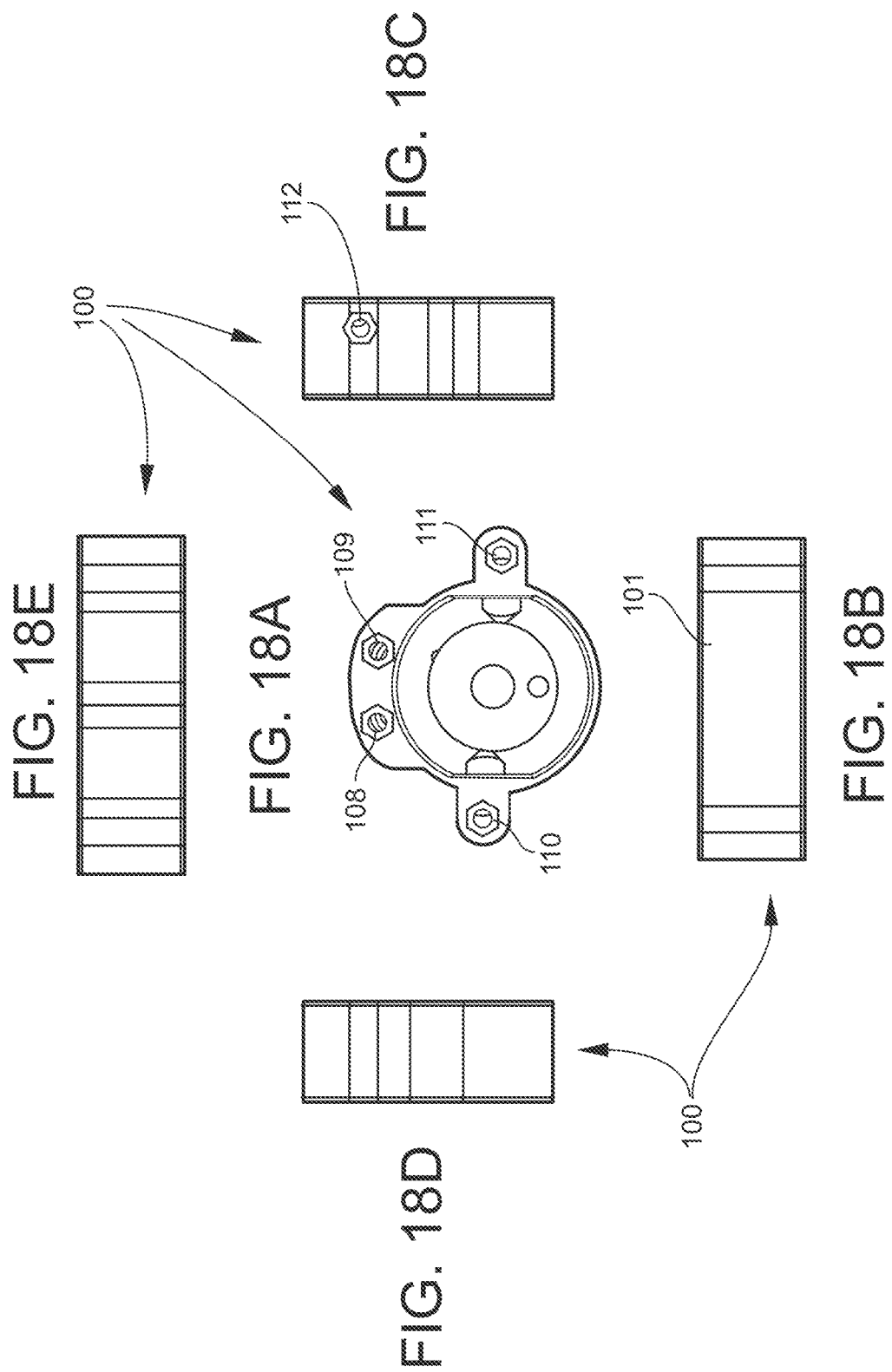

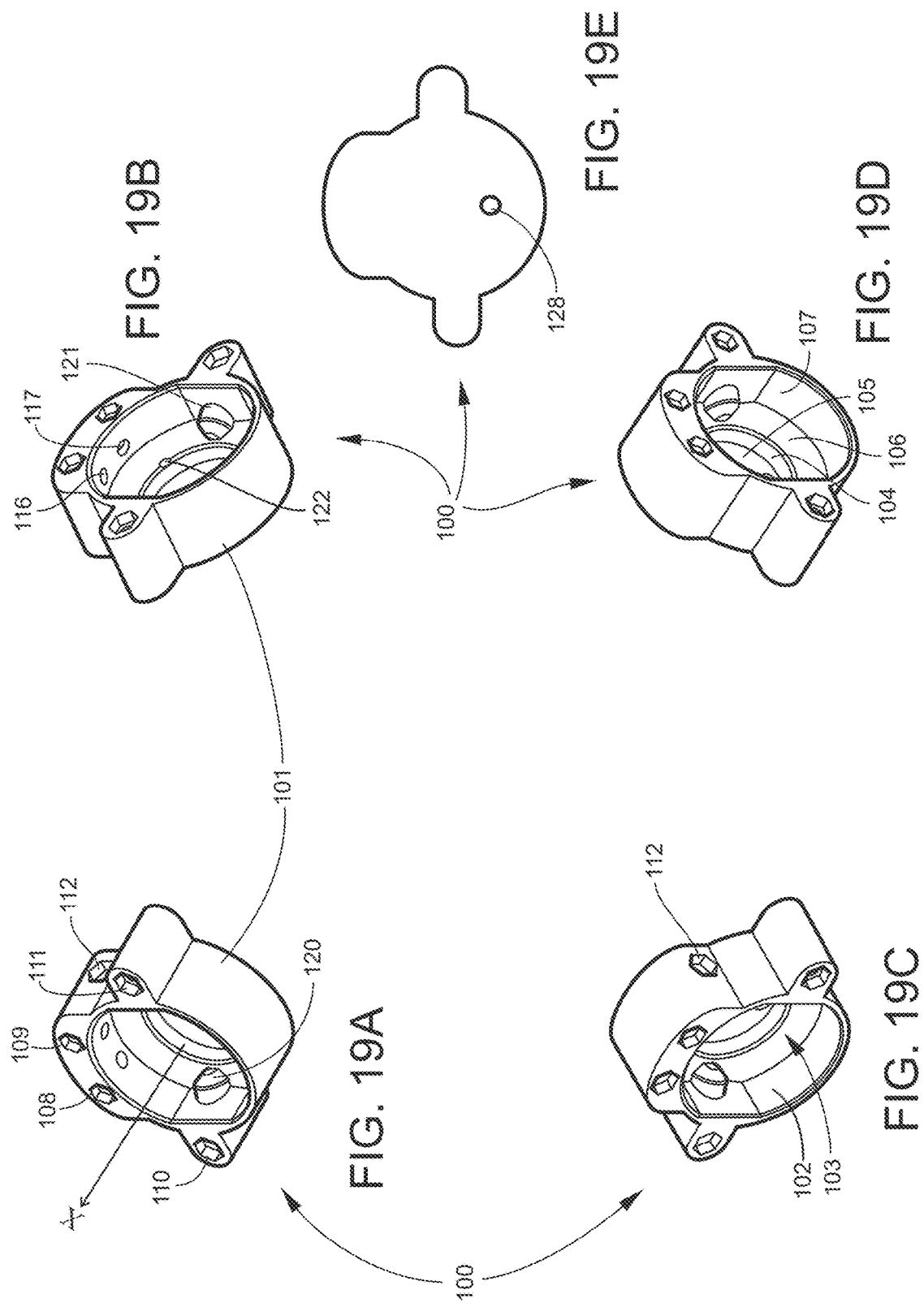

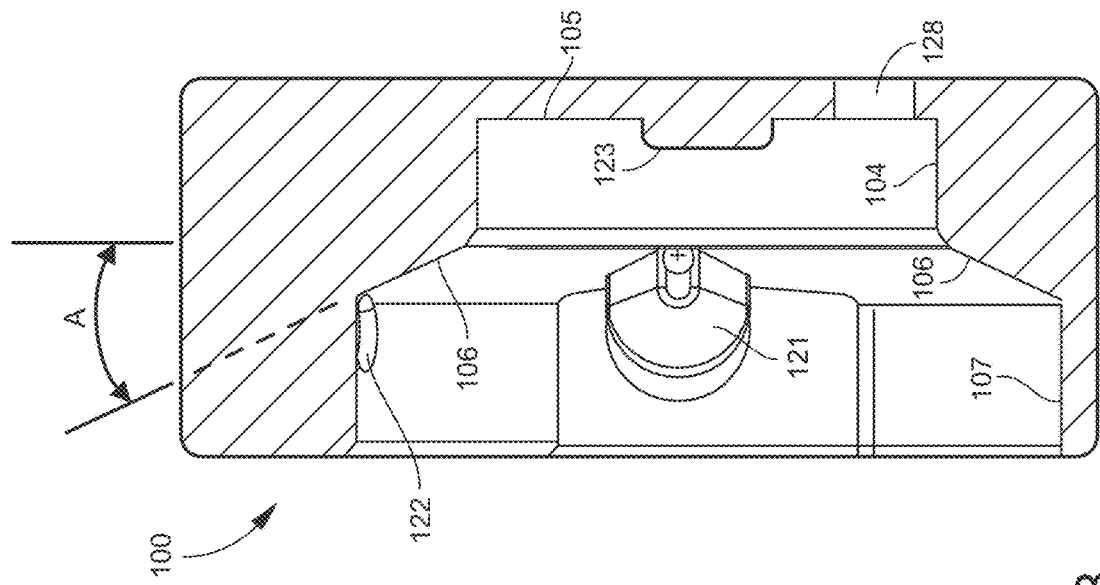
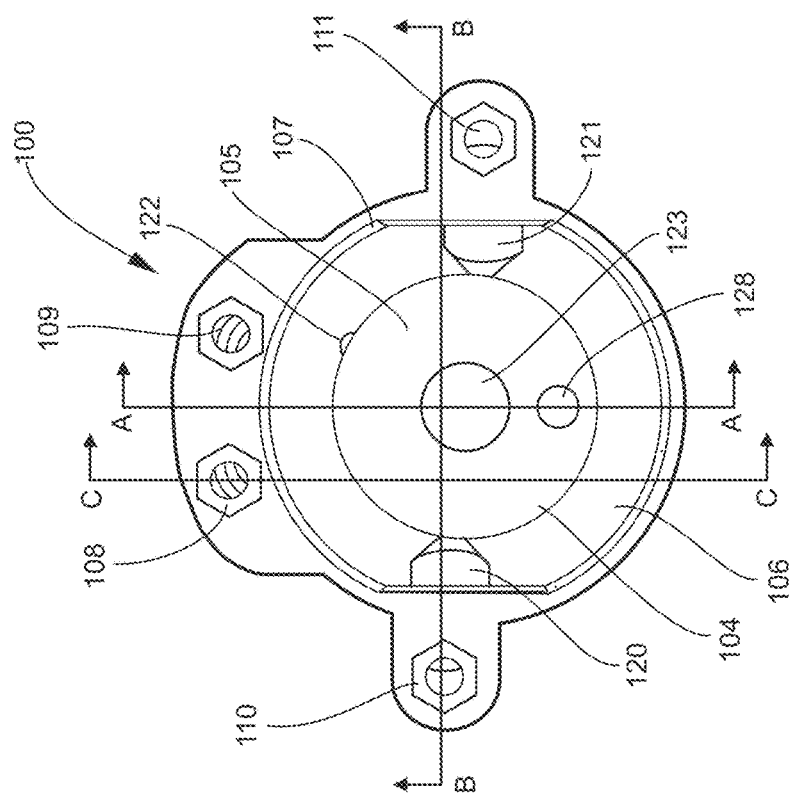
FIG. 20A
FIG. 20B

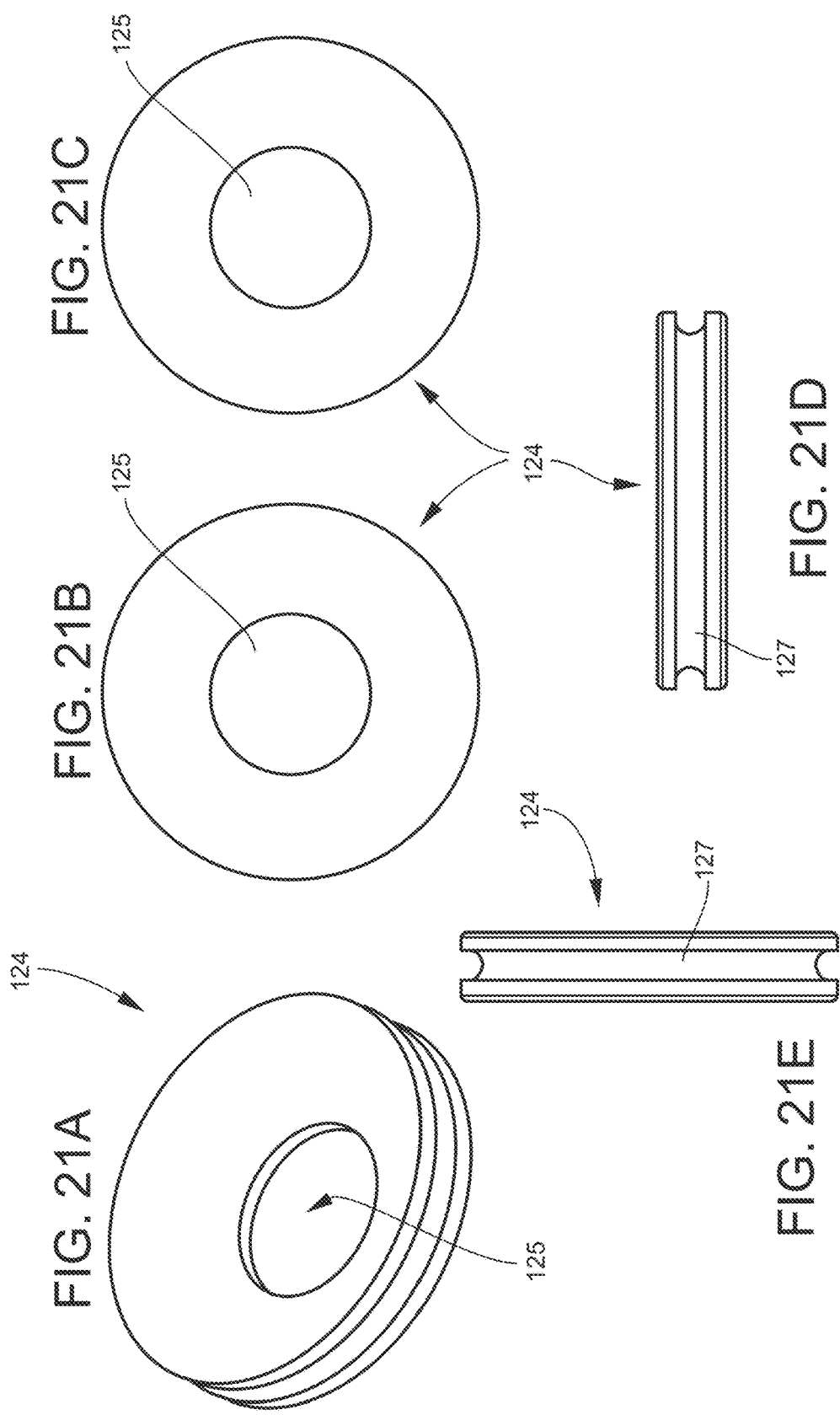

DEVICE AND METHOD FOR ISOLATION OF CORNEAL ENDOTHELIAL CELLS

STATEMENT OF GOVERNMENT INTEREST

The invention described herein may be manufactured, used and licensed by or for the United States Government.

BACKGROUND OF THE INVENTION

The invention relates in general to the isolation of certain types of animal cells and in particular to the isolation of specific types of cells found in the eye.

FIG. 8 is a side sectional view of a human eye 28. The eye 28 has a lens 30 and a cornea 32. FIG. 9 is an enlarged sectional view of the cornea 32. Mammalian corneal endothelial cells (CECs) 34 are a single layer of cells located on the posterior side of the cornea 32, facing the anterior chamber. The outermost layer of the cornea 34 is the epithelium 36. CECs 34 allow nutrients from the anterior chamber to pass into the cornea 32. CECs 34 pump water out of the cornea 32 and into the anterior chamber. CECs 34 in the intact adult human eye have limited growth potential. CECs demonstrate highly limited growth potential in vivo. A reduction in CEC number is normally observed during aging, but this is usually accommodated for by an increase in average cell diameter.

If a critical number of CECs are lost due to disease or injury, this compensatory response is no longer sufficient, and the endothelial barrier is breached. Subsequent corneal edema results in significant inflammation, epithelial bullae, and limbal stem cell deficiency. Together these complications can eventually lead to corneal opacity and total vision loss. The best characterized examples of CEC loss include Fuch's dystrophy (a genetically-based degenerative disease of the corneal endothelium), aphakic/pseudophakic bullous keratopathy (PBK, resulting from endothelial cell injury incurred during cataract surgery) and mustard gas keratopathy (MGK, which occurs following ocular exposure to the chemical warfare agent sulfur mustard). Surgical intervention by corneal transplant is the only currently available option for patients with critical CEC loss. However, transplantation is often unavailable due to the limited supply of fresh corneas suitable for transplantation. Patients that do receive donated tissue face the possibility of transplant rejection.

A known process for isolating CECs is called Descemet's stripping. This procedure involves the use of a sharp, bladed instrument known as a trephine. The trephine is used to scrape CECs 34 away from the underlying basement membrane 38 (Descemet's Membrane). This method can frequently result in the co-isolation of corneal stromal cells 40 (keratocytes) located beneath Descemet's Membrane 38. Keratocytes 40 have a very high proliferative potential. Therefore, CEC isolation by Decemet's stripping often results in the overgrowth of contaminative keratocytes 40 during cell culture expansion, rendering the expanded cells unusable for transplant or for the study of a homogenous CEC population.

A need exists for an apparatus and method for isolating pure populations of CECs from a cornea.

SUMMARY OF THE INVENTION

A first aspect of the invention is an apparatus for isolating corneal endothelial cells (CECs). The apparatus includes a housing having an exterior wall and an interior wall that defines a hollow interior of the housing. The hollow interior has a central longitudinal axis. The interior wall of the housing has a lower portion that extends upwardly and generally perpendicular to a circular base, a middle portion that angles upwardly away from the lower portion and an upper portion that extends upwardly from the middle portion. At least four fluid channels are formed in the housing with two of the channels terminating in respective openings in the upper portion of the interior wall and two of the channels terminating in respective jets in the upper portion of the interior wall.

One jet is located circumferentially approximately opposite the other jet. A drain port is formed near an intersection of the middle and lower portions of the interior wall and leads to a fifth fluid channel formed in the housing. A convex projection is centrally located on the circular base and configured to receive an inverted cornea. The apparatus includes a circular insert having an outer circumference configured to mate with the lower portion of the interior wall. The circular insert has an opening therein in which the convex projection projects when the insert is mated with the lower portion of the interior wall.

The apparatus may include a cover that closes the hollow interior of the housing above the fluid channel openings and jets in the upper portion of the interior wall.

A circumferential groove may be formed in the circular insert and an O-ring inserted in the groove to seal the circular insert to the lower portion of the interior wall of the housing.

The circular insert may include a top surface that angles upwardly from the opening in the circular insert to a circumference of the circular insert. The angle between the top surface of the circular insert and the horizontal may be in a range of about 25 degrees to about 45 degrees.

A second aspect of the invention is a method for isolating corneal endothelial cells (CECs) that includes providing the above-described apparatus of the first aspect of the invention and providing a cornea. The cornea is placed with its endothelial side up over the convex projection. The circular insert is mated with the housing such that the convex projection extends into the opening of the insert and an endothelial layer of the cornea contacts an entire circumference of the opening of the insert. Only the endothelial layer of the cornea is exposed to the hollow interior above the circular insert.

A third aspect of the invention is an assembly that includes the above-described apparatus of the first aspect of the invention and a first fluid container connected to the respective jets in the housing via first and second tubing. First and second pump/motor devices are inserted in the first and second tubing for moving fluid from the first fluid container to the jets. Second and third fluid containers are connected to the respective openings in the upper portion of the interior wall via third and fourth tubing. Third and fourth pump/motor devices are inserted in the third and fourth tubing for moving fluid from the second and third containers to the respective openings in the upper portion of the interior wall. A fourth fluid container is connected to the drain port and the fifth fluid channel in the housing via fifth tubing. A fifth pump/motor device is inserted in the fifth tubing for moving fluid that contains CECs from the housing to the fourth fluid container. A microprocessor controller is connected to each of the five pump/motor devices.

The assembly may include a cover that closes the hollow interior of the housing above the fluid channel openings and jets in the upper portion of the interior wall.

The assembly may include isotonic solution in the first fluid container, trypsin in the second fluid container and dispase in the third fluid container. The fluid containing CECs that is drained from the interior of the housing may be stored in the fourth fluid container.

A bottom surface of the fourth fluid container may includes polycarbonate (PC) plastic.

The invention will be better understood, and further objects, features and advantages of the invention will become more apparent from the following description, taken in conjunction with the accompanying drawings.

BRIEF DESCRIPTION OF THE DRAWINGS

In the drawings, which are not necessarily to scale, like or corresponding parts are denoted by like or corresponding reference numerals.

FIGS. 15A and B are schematic views of a full cone spray nozzle and spray pattern.

FIGS. 16A and B are schematic views of a hollow cone spray nozzle and spray pattern.

FIGS. 17A and B are schematic views of a flat fan spray nozzle and spray pattern.

FIGS. 18A, 18B, 18C, 18D and 18E are top, bottom end, right side, left side and top end views, respectively, of an embodiment of a housing for a device for isolating CECs.

FIGS. 19A-D are perspective views and FIG. 19E is a bottom view of the housing of FIGS. 18A-E.

FIG. 20A is a top view of the housing with lines for sectional views.

FIG. 20B is a sectional view along the line AA of FIG. 20.

FIGS. 21A, 21B, 21C, 21D and 21E are perspective, top, bottom, horizontal side and vertical side (rotated 90 degrees from FIG. 21D) views of an insert for the housing of FIGS. 18A-E.

DETAILED DESCRIPTION

When donated corneas are available, CECs may be isolated from the corneas and the number of CECs expanded by in vitro culture. The CECs may then be frozen. The Human Leukocyte Antigen (HLA) profile may be used to determine the immunologic compatibility of the donor for each batch of frozen CECs. Cyro-preserved CEC stocks may then be available for transplant to immunologically compatible patients.

Figure 1:
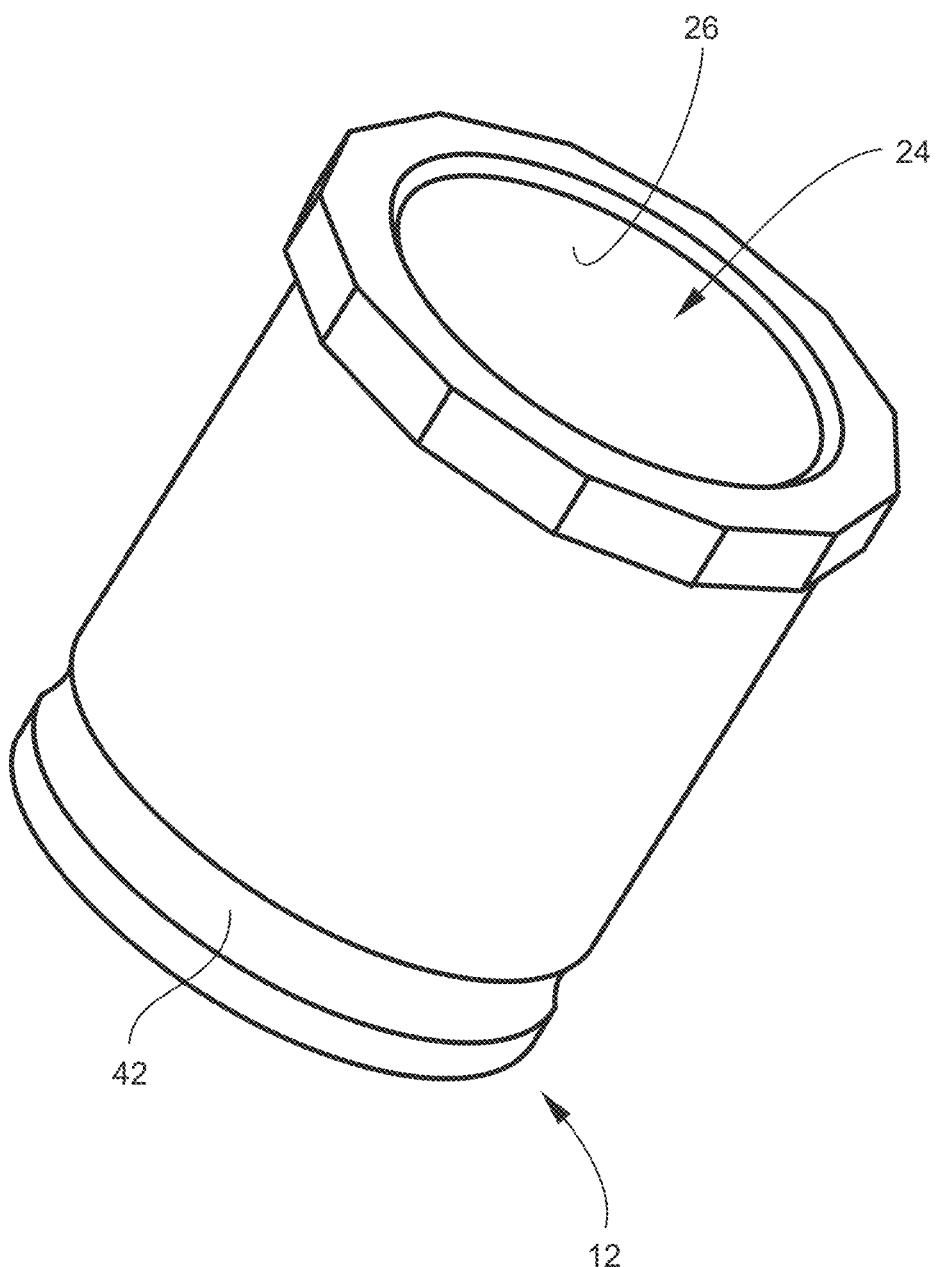
FIG. 1 is a side perspective view of a top portion of one embodiment of a device for isolating CECs.
Figure 2:
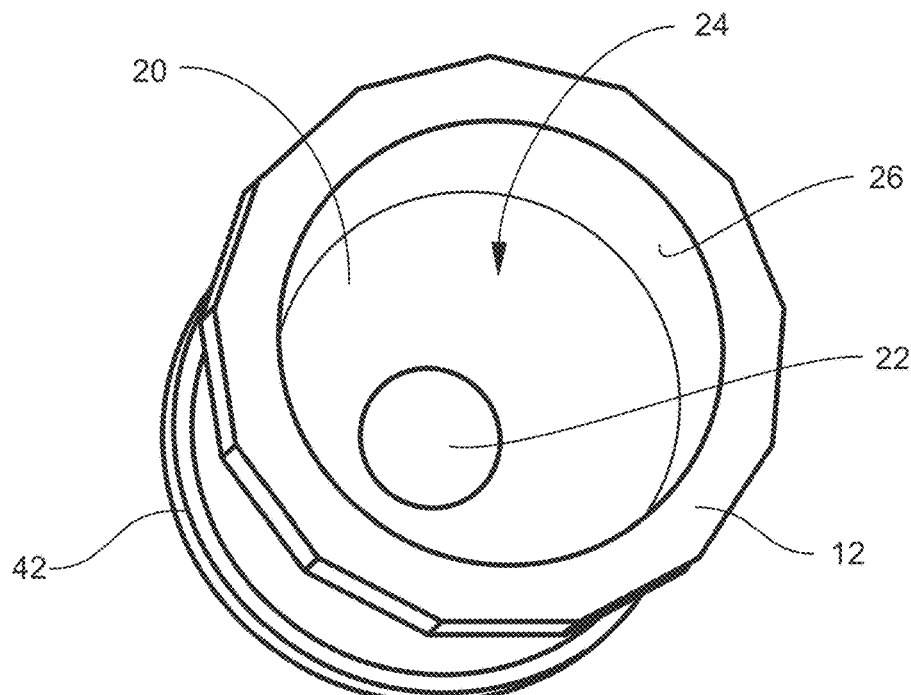
FIG. 2 is a top perspective view of FIG. 1.
Figure 3A:
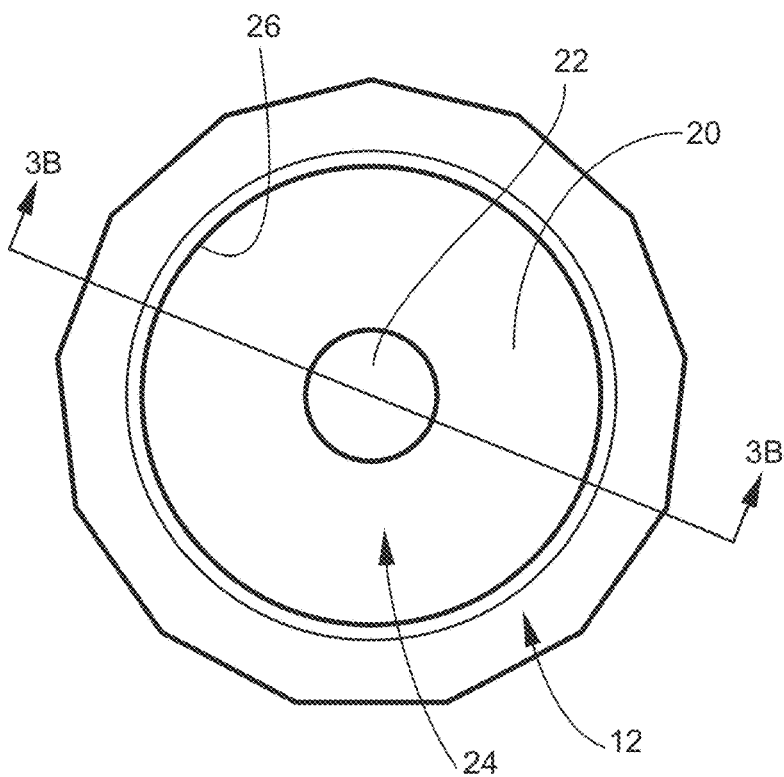
FIG. 3A is a top view of FIG. 1.
Figure 3B:
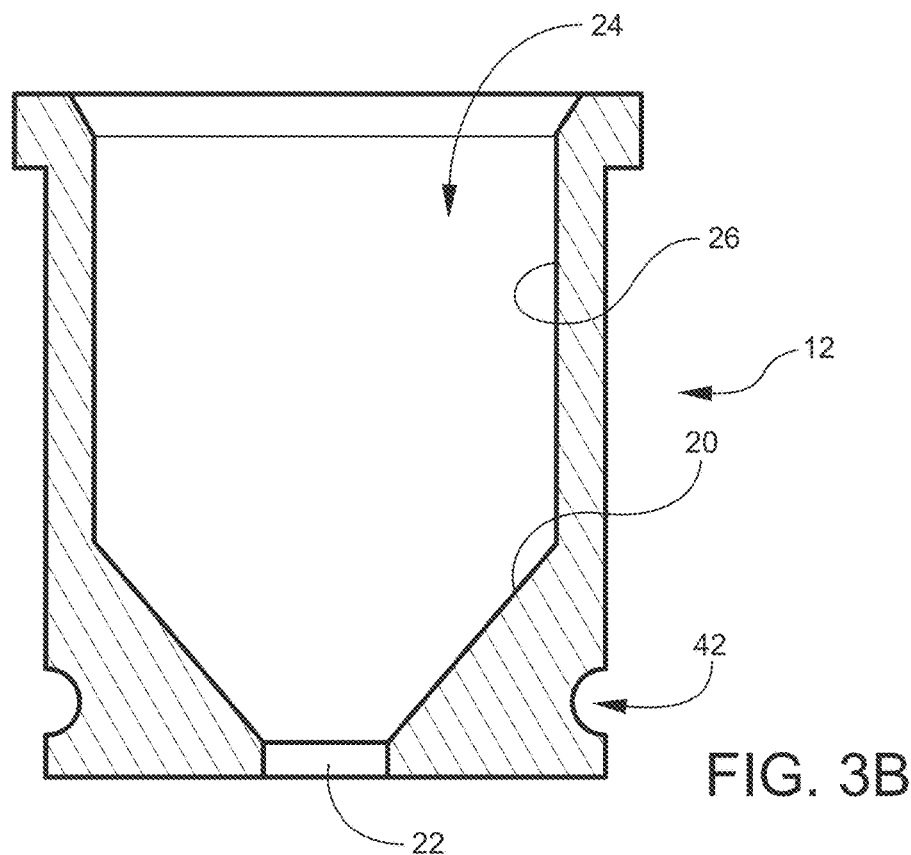
FIG. 3B is a sectional view taken along the line 3B-3B of FIG. 3A.
Figure 4:
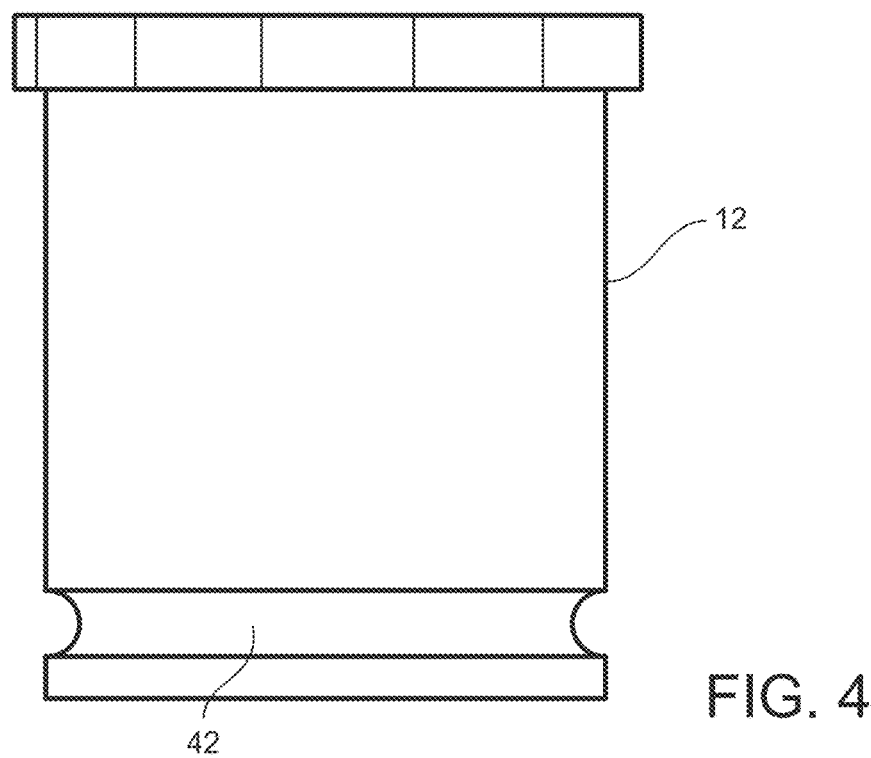
FIG. 4 is a side view of FIG. 1.
Figure 5:
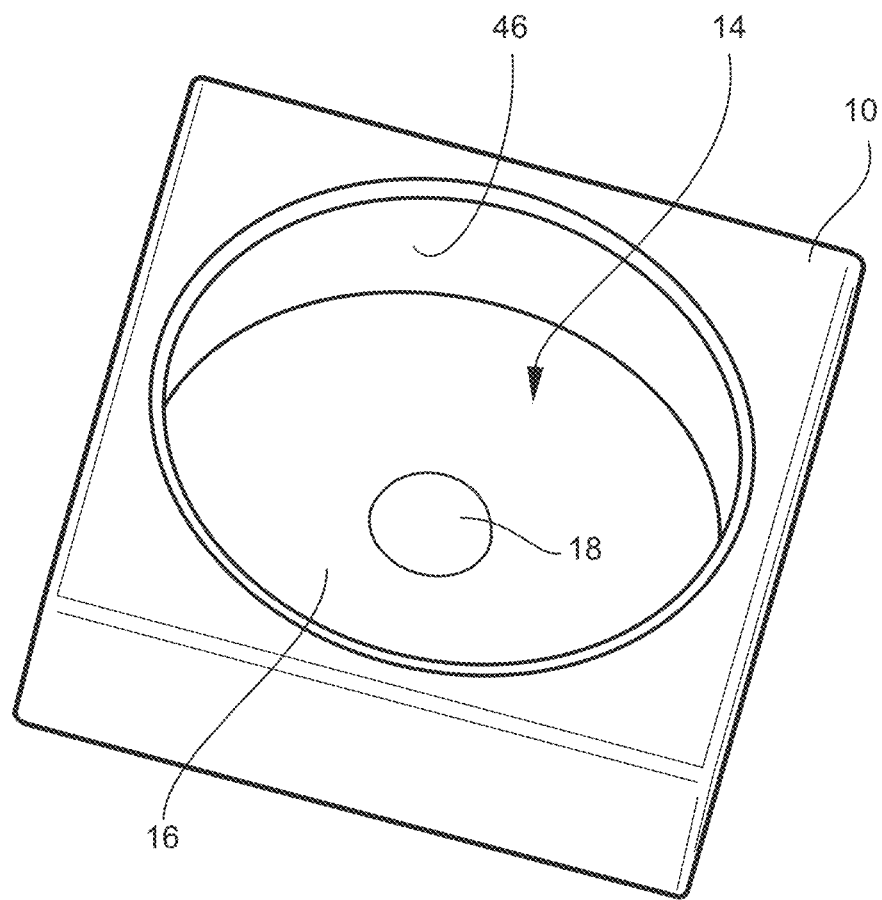
FIG. 5 is a perspective top view of a base portion of one embodiment of a device for isolation CECs.
Figure 6A:
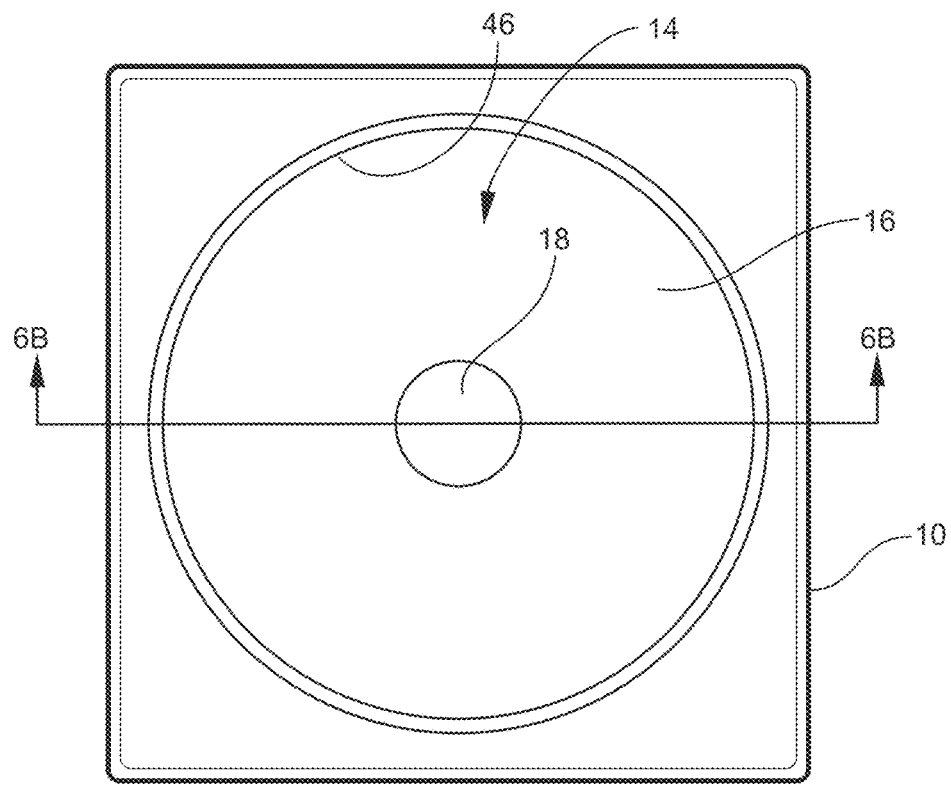
FIG. 6A is a top view of FIG. 5.
Figure 6B:
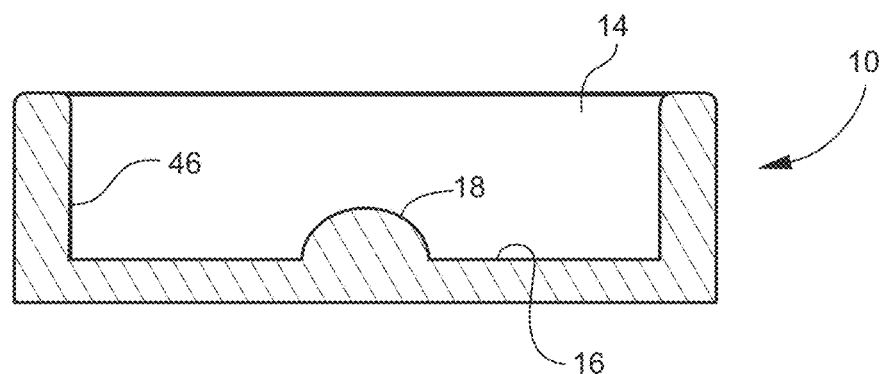
FIG. 6B is a sectional view taken along the line 6B-6B of FIG. 6A.
Figure 7:
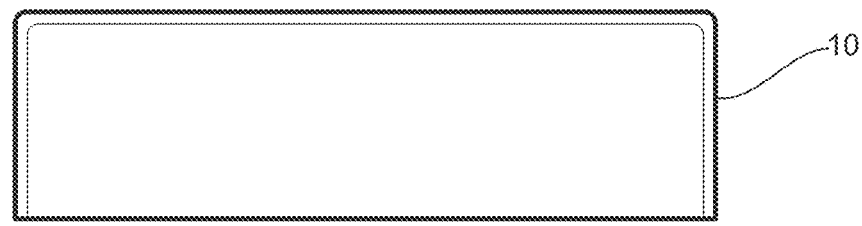
FIG. 7 is a side view of FIG. 5.
Figure 8:
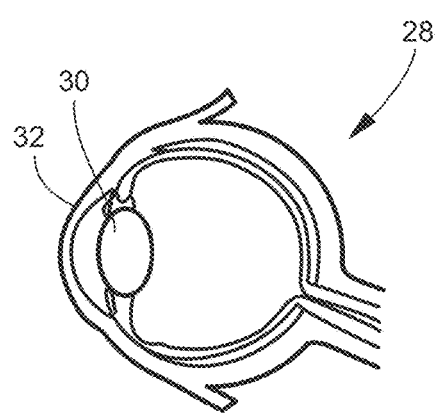
FIG. 8 is a side sectional view of a human eye.
Figure 9:
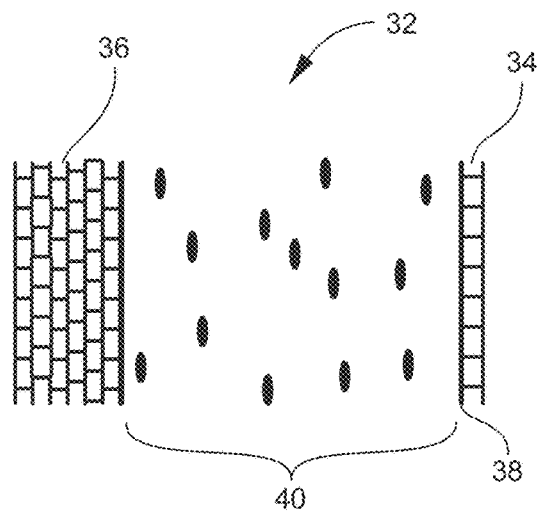
FIG. 9 is an enlarged sectional view of a cornea.

A novel device 8 (FIG. 11) for isolating CECs includes a base portion 10 (FIGS. 5-7) and a top portion 12 (FIGS. 1-4) that fits on the base portion 10. The base portion 10 has an interior recessed opening 14 with a bottom surface 16. A convex projection 18 is centrally located on the bottom surface 16 and configured to receive an inverted cornea 32 (FIGS. 8 and 9). That is, the epithelium 36 is placed in contact with the convex projection 18 so that the endothelium 34 faces upward away from the base portion 10. In this condition, the cornea 32 is in a state of curvature that is opposite its natural state of curvature shown in FIG. 8.

Figure 11:
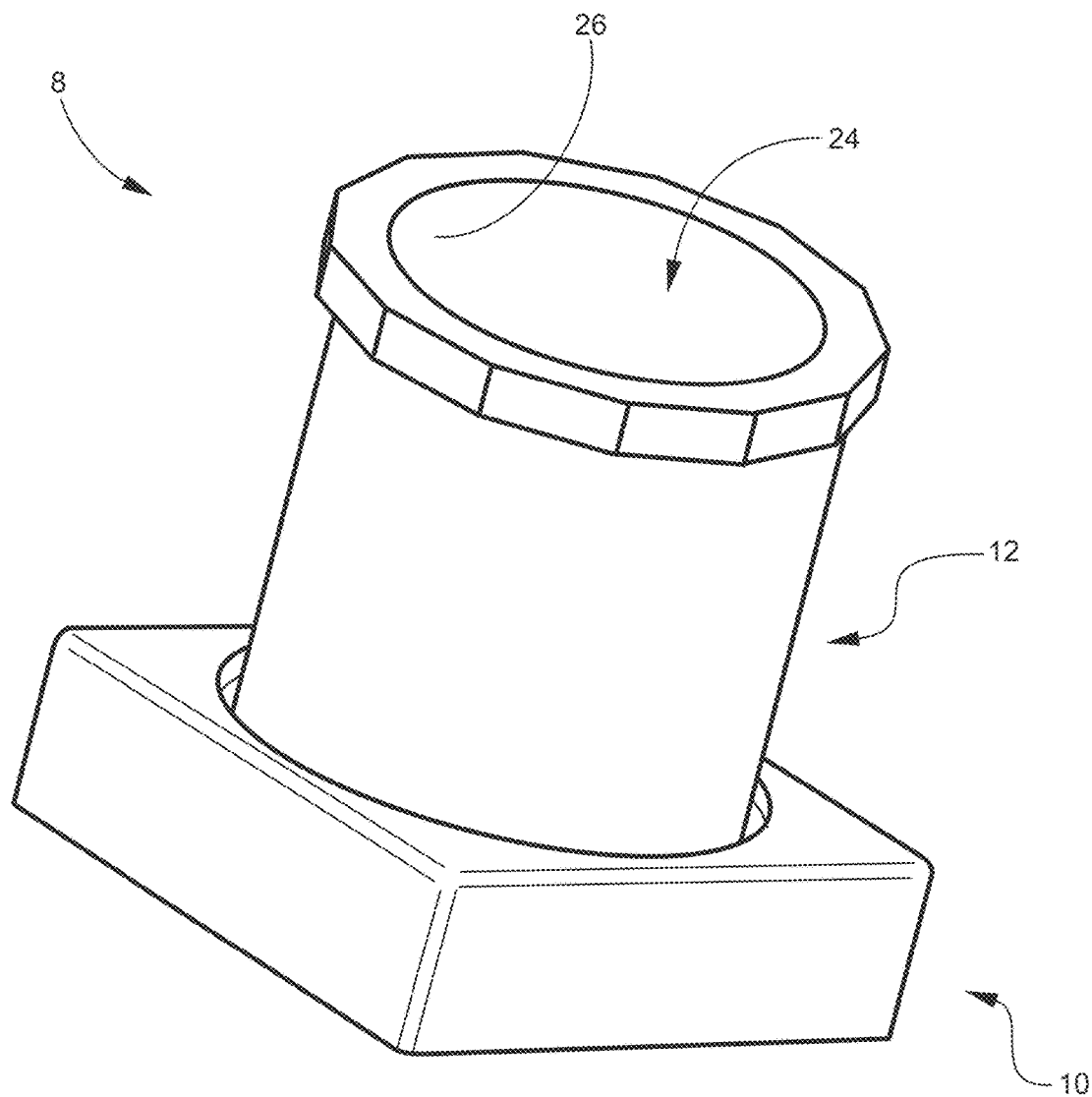
FIG. 11 is a perspective view of an isolation device showing the top portion of FIG. 1 assembled to the base portion of FIG. 5.

The top portion 12 is configured to mate with the base portion 10 (see FIG. 11). The top portion 12 includes a fluid chamber 24 with a lower surface 20. The lower surface 20 has a central opening 22 therein in which the convex projection 18 projects when the top portion 12 is mated with the base portion 10. The lower surface 20 of the top portion 12 extends from and angles up and away from the opening 22 and joins a side wall 26 of the top portion 12. The angle of the lower surface 20 with the horizontal may be in a range of about 30 degrees to about 70 degrees. Preferably, the angle of the lower surface 20 with the horizontal is in a range of about 40 degrees to about 60 degrees. More preferably, the angle is about 50 degrees.

Figure 10:
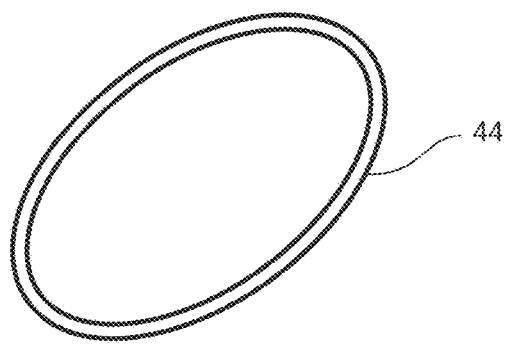
FIG. 10 is a perspective view of an O-ring.

The inverted cornea 32 is placed on the convex projection 18 and forms a fluid seal between the fluid chamber 24 of the top portion 12 and the interior recessed opening 14 of the base portion 10. Only the endothelial surface 34 of the inverted cornea 32 is exposed to the fluid chamber 24. A groove 42 may be formed on a lower exterior circumferential surface of the top portion 12. An O-ring 44 (FIG. 10) may be disposed in the groove 42. The O-ring 44 may provide a friction fit between the top portion 12 and a side surface 46 of the opening 14 in the base portion 10. O-ring 44 stabilizes top portion 12 on base portion 10 and thereby contributes to the fluid seal formed by the inverted cornea 32. In addition, in the event any fluid leaks past cornea 32, O-ring 44 contains the leaked fluid in base portion 10.

A plurality of the top portions 12 may be provided. The opening 22 in each top portion 12 may have a different diameter. The differing diameters of the openings 22 may be used to accommodate different size corneas, for example, corneas from different species of animals. For a guinea pig cornea, the diameter of opening 22 may be, for example, 7 mm. For a human cornea, the diameter of opening 22 may be, for example, 11.5 mm. The diameter of opening 22 is set to be equal to the diameter of the cornea. The cornea may be slightly stretched to account for minor differences in the diameter of the cornea in the vertical and horizontal direction. Slightly stretching the cornea may be advantageous because it facilitates degradation of the CEC attachment sites by enzymes.

The height of the convex projection 18 may vary with the height of the cornea as measured from the cornea center to the cornea periphery. This adjustment is necessary because corneas from different species cover different percentages of the eye globe. For example, porcine corneas occupy a smaller percentage of the porcine eye globe compared to the percentage that a guinea pig cornea covers a guinea pig eye globe. In other words, the periphery of the guinea pig cornea extends further back toward the eye socket than the periphery of the porcine eye globe.

The base and top portions 10, 12 are configured for printing by a 3D printer. The 3D printable design is particularly advantageous in that the same basic design of the isolation device 8 can be utilized for different species, with slight alterations in the diameter of opening 22 and the diameter and height of projection 18. These changes can be made in the computer-assisted drawing (CAD) file that defines each device component before export to a machine capable of 3D printing. Multiple copies of the isolation device 8 can be readily manufactured according to need. Isolation device 8 may be 3D printed using a material such as, for example, polylactic acid. Polylactic acid can be sterilized using low temperature processes such as alcohol immersion or ethylene oxide exposure. If high temperature sterilization methods such as autoclaving are desired, a 3D printer capable of printing with metallic material may be used to manufacture isolation device 8.

The method of using the isolation device 8 includes placing a cornea 32 with its endothelial side 34 up over the convex projection 18. The top portion 12 is mated with the base portion 10 such that the convex projection 18 extends into the opening 22. The endothelial layer 34 of the cornea 32 contacts the entire circumference of the opening 22. Only the endothelial layer 34 will be exposed to the fluid in the fluid chamber 24 of the top portion 12. Proteolytic enzymes that degrade CEC attachment sites, for example, trypsin and dispase, may be added to the fluid chamber 24. The fluid chamber 24 in top portion 12 functions as a chamber or container for containment of the enzymatic digestion solutions.

The total volume of the fluid chamber 24 is in a range of about 2 milliliters to about 12 milliliters, although larger volumes may be used. In one embodiment, the total volume of fluid chamber 24 is about 10 milliliters. The volume of enzymatic solution contained in chamber 24 may be in a range of about 2 milliliters to about 8.5 milliliters. When automated components are used, as discussed in detail below, the maximum volume of solution in the chamber 24 is the total volume of the chamber 24. Following incubation in the presence of the enzyme(s), CECs are easily released from the remaining cornea by repeated pipetting of enzymatic solution. The CECs may then be isolated from the suspension by centrifugation. The isolated CECs may then be grown in culture. For example, the isolated CECs may be grown for six days. The grown CECs may then be frozen.

Test Results

A. CEC Isolation-Two Pig Eyes. Feb. 5, 2015.

Setup:

Dispase II: Add 340 mg to 20 mL complete DMEM/F12 containing 10% FBS and 2×antibiotic/antimycotic. Place in 37 degree C. bath. Aliquot out 100 mL sterile PBS+a.a. for 1 day use. Add 1 mL a.a. to make a total of 2×a.a. Set out two 15 cm dishes, scalpel blade. Sterilize medium pointed scissors, non-serrated sharp narrow forceps, serrated narrow forceps. Sterilize cornea cell isolation devices in 70% ethanol and let dry. Coat T-75 flask with collagen IV. Use 394 ul collagen IV stock into 7.5 mL FBS.

Initial Dissection:

Working in a 15 cm dish containing enough PBS to keep tissues moist, dissect out the cornea plus 2-3 mm of surrounding sclera. It is convenient to use a scalpel for initial cut and scissors for remaining corneal removal.

Enzyme Digestion:

Lay cornea endothelium side up on device base. Push upper chamber of cornea cell isolation device into the lower base over cornea such that only the endothelium is exposed. Add 1 mL 0.25% pre-warmed trypsin to chamber. Place in incubator at 37 degrees C. for 5 minutes. Add 5 mL Dispase II to each corneal cell isolation device and cover with petri dish lid. Place in incubator at 37 degrees C. for 1 hour. After 1 hour incubation, pipette Dispase II solution repeatedly over endothelium surface to bring cells into suspension. Combine and transfer suspension to 15 mL conical tube. Pellet by centrifugation at 500×g for 10 minutes. Aspirate supernatant. Loosen pellet. Re-suspend in 20 mL Proulx medium+25 ug/mL+20 ul gentamycin.

B. CEC Isolation-Four Pig Eyes. Feb. 13, 2015.

Day 1—Corneal Isolation.

Setup:

Set out two 15 cm dishes, scalpel blade, sterile forceps, scissors.

Cornea Dissection:

Working in a 15 cm dish containing enough PBS to keep tissues moist, dissect out the cornea plus 2-3 mm of surrounding sclera. It is convenient to use a scalpel for initial cut and scissors for remaining corneal removal. Add to 20 mL complete DMEM/F12+1:1000 gentamycin in a 10 cm dish and leave o/n at 37 degrees C.

Day 2—CEC Isolation.

CEC Isolation Setup:

Sterilize 4 cornea cell isolation devices in 70% ethanol and let dry in cell culture hood. Dispase II: Add 680 mg to 40 mL complete DMEM/F12 containing 10% FBS and 2×antibiotic/antimycotic. Place in 37 degree C. water bath. Aliquot out 100 mL sterile PBS+a.a. for 1 day use. Add 1 mL a.a. to make a total of 2×a.a. Coat two T-75 flasks with collagen IV. Use 800 uL collagen IV stock into 15 mL PBS. Add 7.5 mL/flask and leave at 37 degrees C. for at least 1 hour.

Enzyme Digestion:

Lay cornea endothelium side up on device base. Snap upper chamber of cornea cell isolation device over cornea such that only the endothelium is exposed. Add 2 mL 0.25% pre-warmed trypsin to chambers. Place in incubator at 37 degrees C. for 5 minutes. Add 10 mL Dispase II solution to each corneal cell isolation device and cover with petri dish lid. Place in incubator at 37 degrees for 1 hour. After 1 hour incubation, pipette Dispase II solution repeatedly over endothelium surface to bring cells into suspension. Combine and transfer suspension to 15 mL conical tube. Pellet by centrifugation at 500×g for 10 minutes. Aspirate supernatant. Loosen pellet. Re-suspend in 40 mL Proulx medium+

32 ul FGF at 25 ug/mL. Rinse collagen IV-coated flasks once with PBS. Add 20 mL cell suspension to each flask and place in 37 degree C. incubator.

Yield Calculation:

The isolated CECs were grown for six days in culture, and then divided to 30 vials for storage in liquid nitrogen. On Feb. 24, 2015, two vials from this batch were thawed and counted to be used in an experiment to compare two different cell growth medium formulations. Each vial was thawed and counted separately. The average number of live cells recovered was calculated to equal 810,000 cells per vial. Assuming each vial has 810,000 live cells, the total number is 30×810,000 or 24,000,000 CECs. Given that four porcine corneas were utilized, 6,000,000 CECs per porcine cornea may be obtained after six days of culture.

Embodiments of the Invention with Automation

The utility of the apparatus 8 may be enhanced with additional components. These components enable additional functions and features. One additional feature is automated fluid delivery so that enzymatic solutions can be delivered to the fluid chamber 24 in accordance with specific user-defined volumes and speeds. A second additional feature is uniform wash of the endothelial surface. Pressurized fluid is delivered to the endothelial surface through a "full cone" nozzle that results in high flow rates consistent in force over the entire endothelial area. A third additional feature is automated sample collection wherein cell isolates are collected in a conical centrifuge tube ready for further processing. A fourth additional feature is programmable process control. Precise control of incubation timing and fluid force is enabled by incorporating a programmable microcontroller (circuit board with minimal operating system) into the assembly.

Automated Fluid Delivery

With automated fluid delivery, addition of an enzymatic solution to the fluid chamber 24 is performed automatically with a pump or pumps. Typically, the enzymatic solution is Dispase II in DMEM/F12+10% FBS. After the enzymatic solution digests the endothelial surface, repeated manual pipetting of the solution onto the endothelial surface to bring the CECs into suspension is not required. All the process steps, from reagent addition to resuspension of the pelleted isolate into growth medium are achieved in a closed system. Tissues and cell suspensions remain within sealed enclosures and tubing during isolation steps. Closed system processing is generally required in clinical manufacturing to minimize the risk of microbial contamination of the finished product. Tissues and cell suspensions remain within sealed enclosures and tubing during isolation steps.

Figure 12:
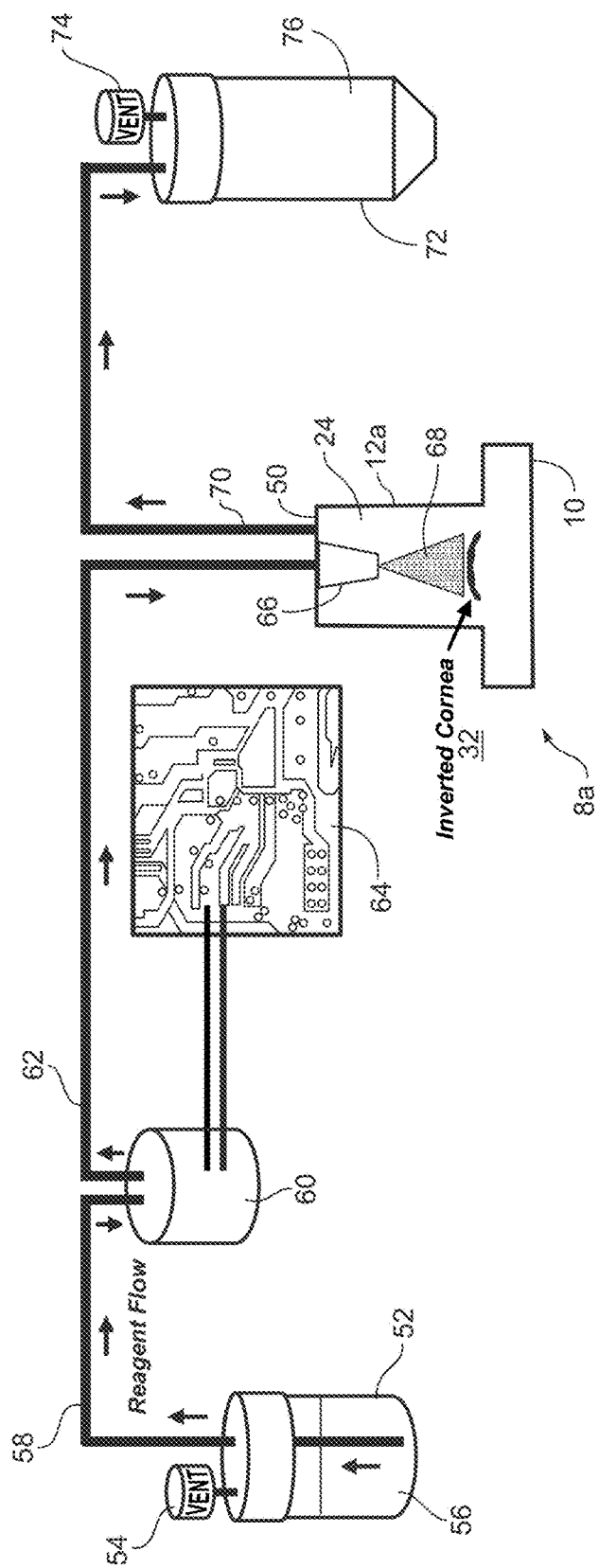
FIG. 12 is a schematic diagram of one embodiment of an automated apparatus for isolation of endothelial cells.
Figure 13:
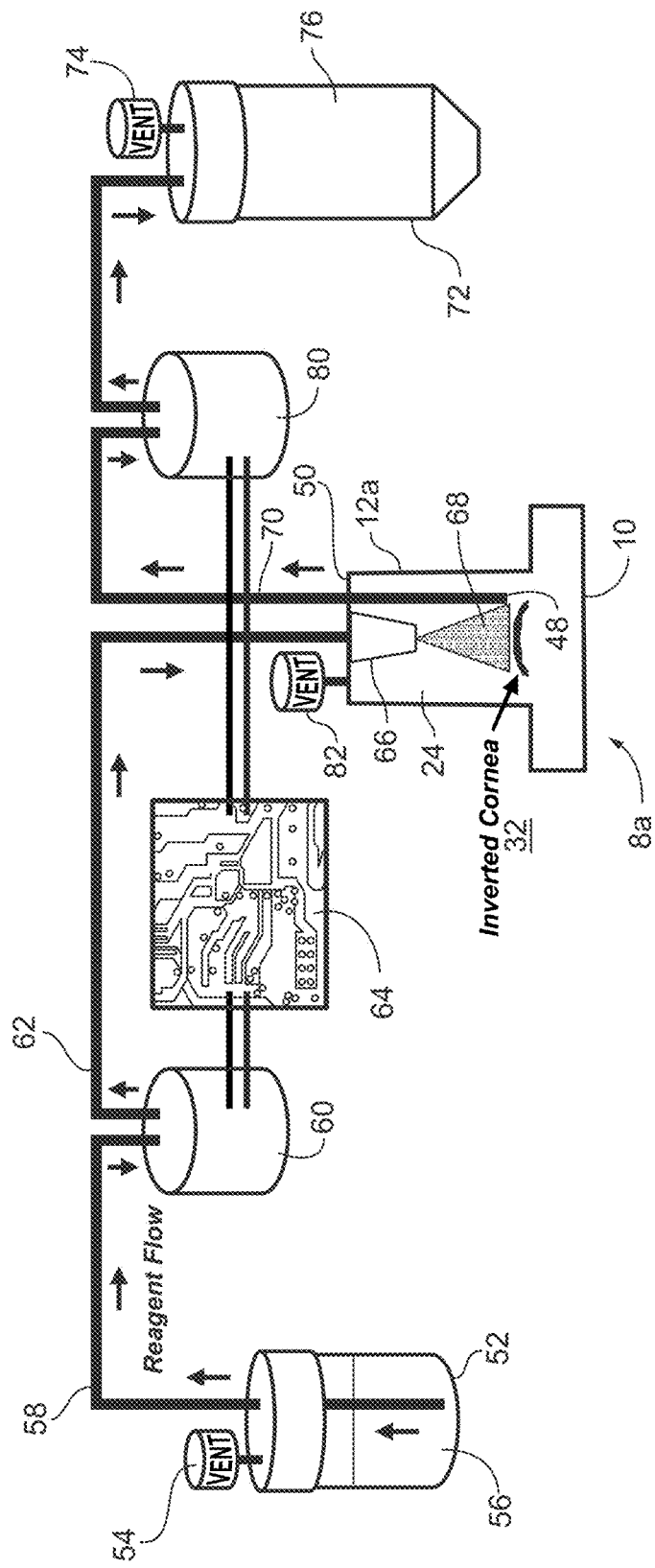
FIG. 13 is a schematic diagram of a second embodiment of an automated apparatus for isolation of endothelial cells.
Figure 14:
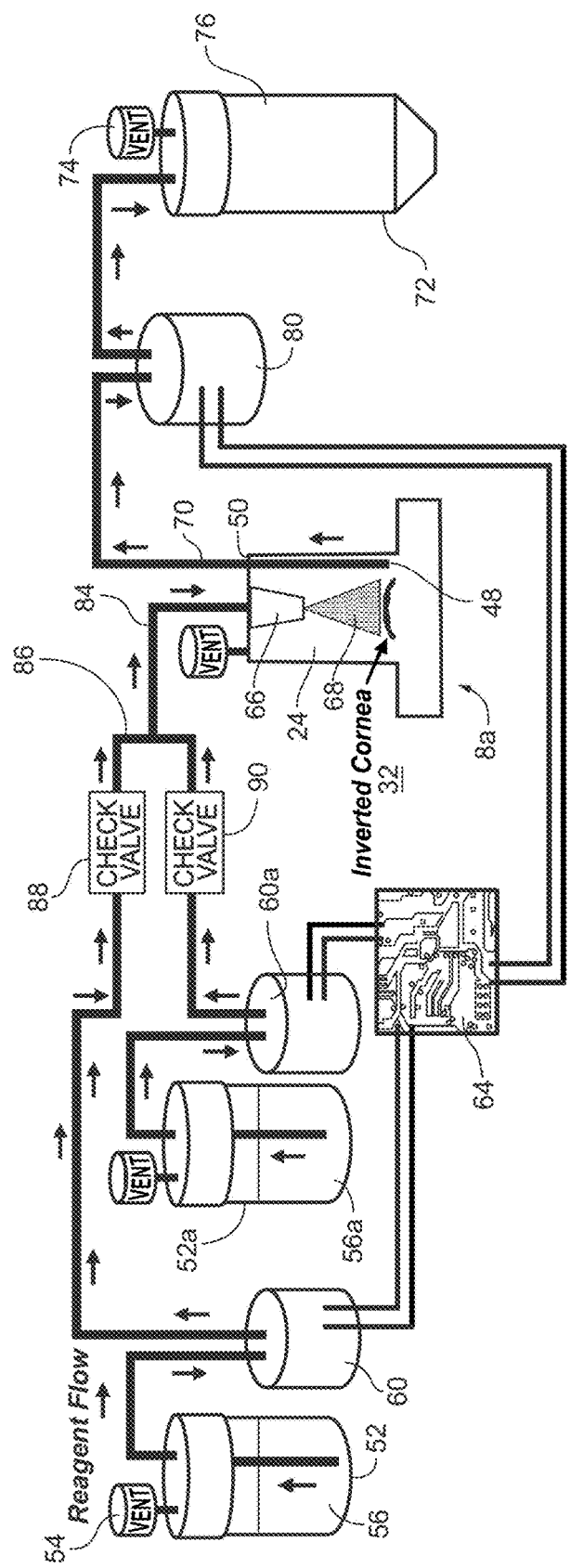
FIG. 14 is a schematic diagram of a third embodiment of an automated apparatus for isolation of endothelial cells.

FIGS. 12-14 are schematic diagrams of three exemplary embodiments of an automated assembly for isolation of endothelial cells.

Referring to FIG. 12, a reagent reservoir 52 contains reagent 56. Reagent 56 may be, for example, Dispase II in DMEM/F12+10% FBS. Reservoir 52 may have a volume of, for example, 10 milliliters. A vent 54 vents reservoir 52. Tubing 58 carries reagent from reservoir 52 to peristaltic pump 60. Tubing 62 carries reagent 56 from pump 60 to isolation assembly 8a. Tubing 70 carries reagent 56 with endothelial cells 34 from isolation assembly 8a to collection tube 72. Collection tube 72 is preferably a conical centrifuge tube. Tube 72 may have a volume of, for example, 50 milliliters. Isolation assembly 8a is similar to isolation assembly 8 shown in FIGS. 1-7 and 11.

Isolation assembly 8a differs from assembly 8 by the addition of a closed lid 50 on top portion 12a. Lid 50 has openings for tubing 62 and 70. A full cone spray nozzle 66 (FIGS. 15A and B) is fixed to the underside of lid 50. Full cone spray nozzle 66 produces a spray pattern 78 shown in an angled side view in FIG. 15A and in a bottom view in FIG. 15B.

Reagent fluid 56 is moved from reagent reservoir 52 through fluid chamber 24 in isolation assembly 8a by peristaltic pump 60. Pump 60 may operate at 12 volts or 24 volts. Pump 60 may have a maximum flow rate of 200 to 500 milliliters per minute, for example. Pump 60 generates directional flow through rhythmic compressions of fluid-filled tubing. Peristaltic pumps are designed to maintain the separation of sterile fluids within the tubing from mechanical pump components. The reservoir 52 is sterilely vented with vent 54 to release negative pressure that would otherwise accumulate as fluid 56 is pumped out of the reservoir. An electronic microcontroller 64 switches pump 60 on and off, controls the speed of reagent flow while the pump 60 is on, and determines the length of time the pump 60 will be in the "on" or "off" state during each step of the process.

Corneal tissue 32 is seated in the base portion 10 of the isolation device 8 a with the CECs 34 facing upward into chamber 24. Corneal tissue 32 may be incubated in enzymatic solutions at user-defined time periods. After the chamber 24 is filled with enzyme solution, the pump 60 may be placed in the "off" state by the microcontroller 64. The length of time that the pump 60 is in the "off" state can be adjusted to obtain maximal CEC yield.

To detach CECs 34 from the remaining cornea, the microcontroller 64 places the pump 60 in the "on" state and passes reagent 56 through a full cone nozzle 66 at a relatively high flow rate. The resulting high-pressure fluid flow facilitates CEC release from underlying corneal tissue and brings the cells into suspension. The detached, suspended CECs 34 are forced through a final tubing segment 70 that connects the isolation device 8a to a vented collection tube 72. The tube vent 74 releases positive pressure, allowing forward movement of the cell suspension and deposition into the collection tube 72. The collection tube 72 is preferably of a type that may be directly mounted into a centrifuge.

Referring now to FIG. 13, the assembly of FIG. 13 operates under the same general principles as the embodiment of FIG. 12, but incorporates an additional peristaltic pump 80 situated between the isolation device 8a and the collection tube 72. Microcontroller 64 can operate both pumps 60, 80 simultaneously. The pump 80 provides additional control of fluid 56 through the assembly. The additional pump 80 introduces a compression point in the tubing 70 that connects the isolation device 8a to the collection tube 72. While pump 80 is in the "off" state therefore, fluid movement within the tubing 70 is prevented. This arrangement blocks possible fluid spillage from the isolation device 8a to the collection tube 72, or from the collection tube 72 back into the isolation device 8a.

In FIG. 13, a sterile vent 82 is incorporated within the isolation device 8a. Therefore, when the reagent reservoir pump 60 is in the "off" state and the pump 80 is in the "on" state, the fluid chamber 24 of the isolation device 8 a can be drained at a specific stage in the process. Draining the contents of chamber 24 may be desirable in cases where the enzymatic reagents that are used are costly. For example, with the addition of pump 80, no additional enzyme solution would be required to carry detached CECs 34 out of the chamber 24 and into the collection tube 72, in contrast to the embodiment of FIG. 12. In FIG. 13, the end 48 of tubing 70 extends into the fluid chamber 24 and terminates adjacent the convex projection 18 and inverted cornea 32.

The ability to drain the chamber 24 also enables repeated rinsing of corneal tissue after CECs 34 are suspended by high pressure flow from the full cone nozzle 66. For example, with the reservoir pump 60 off and the pump 80 on, re-suspended cell suspension is delivered to the collection tube 72. If the pump 80 is then turned off and the reagent pump 60 is turned on, fresh solution is delivered to the tissue sample. The rinse solution can in turn be removed and transferred to the collection tube 72 by turning the pump 80 back on while holding the reservoir pump 60 in the off state. A rinse sequence can be repeated multiple times to achieve maximal transfer of residual CECs 34 from the chamber 24 to the collection tube 72.

Referring to FIG. 14, a third embodiment of the CEC isolation assembly enables the use of two distinct reagent fluids 56, 56a during the same operation run. Importantly, the assembly still operates as a closed system. No components of the system must be removed or opened to allow the in-process addition of the second reagent fluid 56a. The pump 80 as described with reference to FIG. 13 is included in the embodiment of FIG. 14.

Incorporation of a second reagent fluid 56 a is achieved by adding a second reagent reservoir 52a and pump 60a to the assembly. A single microcontroller 64 is capable of independently and simultaneously operating all three pumps 60, 60a and 80. Reagent flow from each of the two reservoirs 52, 52a is driven by a corresponding pump 60, 60a (i.e., each reservoir is paired with a dedicated, independently operating pump). Fluid flow from the reservoirs 52, 52a follows a tubing path that converges to a single line 84 via a "Y"-type tubing connector 86 before entering the isolation device 8a.

To ensure delivery of one reagent at a time to the chamber 24, check valves 88, 90 are incorporated into the tubing path just prior to the position of the "Y" connector 86. Check valves 88, 90 are only open to allow fluid flow when fluid pressure is exerted on the respective valve 88, 90. Sequential delivery of two separate reagents 56, 56 a is achieved in the following manner. Pump 60 is switched on by the microcontroller 64, while pump 60a is maintained in the "off" state. As pressure builds in the tubing path maintained by pump 60, the check valve 88 within this path opens. The tubing path operated by pump 60a remains closed since there is no pressure accumulation to open the check valve 90 in the corresponding tubing path.

The microcontroller 64 can be programmed to deliver the first reagent 56 for a set period of time. When the specified time to stop reagent delivery is reached, pump 60 is set to the "off" state, fluidic pressure in the tubing path of pump 60 drops, and the check valve 88 for this path closes. To deliver the second reagent 56a to the chamber 24 of the isolation device 8a, pump 60a is set to "on", while pump 60 is maintained in the "off" state. Pressure within the tubing path for pump 60a increases until the check valve 90 in this path is open. Reagent 56a will now flow into the chamber 24 of the isolation device 8a without prior mixing with reagent 56.

Uniform Wash of the Endothelial Surface

Enzymatic solutions and wash solutions are passed through a "full cone" spray nozzle 66. FIGS. 15A and B are schematic views of a full cone spray nozzle 66 and spray pattern 78. Spray pattern 78 is shown in angled side view in FIG. 15A and in bottom view in FIG. 15B. By way of contrast, FIGS. 16A and B are schematic views of a hollow cone spray nozzle 92 and spray pattern 96 and FIGS. 17A and B are schematic views of a flat fan spray nozzle 94 and spray pattern 98. Spray patterns 96, 98 are shown in angled side views in FIGS. 16A and 17A, respectively, and in bottom views in FIGS. 16B and 17B, respectively. The full cone configuration of FIGS. 15A and B emits a relatively even distribution of flow over the endothelial surface, compared to the hollow cone nozzle 92 (FIGS. 16A and B) or flat fan nozzle 94 (FIGS. 17A and B) configuration.

Automated Sample Collection

Fluids are moved through the processing assembly, terminating with sample collection in a collection or centrifuge tube 72. After the isolated CECs are dispensed in the centrifuge tube 72, the cells can be pelleted by centrifugation, re-suspend in nutrient growth medium and seeded to a cell culture vessel for in vitro expansion of cell number.

Programmable Process Control

Operation of the peristaltic pump(s) utilized in the automated process is determined by signals received from a microcontroller 64, which is a circuit board with a rudimentary operating system. Various microcontrollers are available on the market. In one embodiment, the microcontroller 64 may be a Raspberry Pi brand of microcontroller.

The Raspberry Pi microcontroller can interpret and implement instructions from the simple computer programming language "Python". As an example, Python may be used to control the following process sequence of a single pump 60 in the embodiment of FIG. 12:

(1) Start the flow of enzyme solution 56 from the reagent reservoir 52.
(2) Fill the chamber 24 of the CEC isolation device 8a.
(3) Stop the flow to allow sufficient digestion of CEC-to-DM (Descemet's Membrane) attachment sites (for example 1 hr).
(4) Pulse a high speed (high pressure) flow of additional solution 56 over the endothelial surface to loosen CECs 34 and bring them into suspension (for example, 20 pulses lasting 3 seconds each). Note from FIG. 12 that as flow continues above the volume that can be contained by the fluid chamber 24, excess volume is dispensed into the collection tube 72. Solution 56 from the reagent reservoir 52 will be fed into the system until CECs 34 are dispensed to the collection tube 72.

Also note that varying enzyme digestion times (for example, 1 hour, 1.5 hours, 2 hours) can be programmed into the microcontroller 64. Likewise, the number and pressure of fluid pulses used to free cells from Descemet's Membrane 38 (FIG. 9) can also be varied according to instructions written into Python code. A simplified example of Python code capable of controlling the behavior of a peristaltic pump 60 is shown below. When the below code is executed, the microcontroller 64 will turn on a peristaltic pump 60 (denoted as "motor" in the code) at 100% power. The pump 60 will continue to operate for 30 seconds and then will turn off.

Code:

```
import RPi.GPIO as GPIO
GPIO.setwarnings (False)
GPIO.setmode(GPIO.BOARD)
import time
GPIO.setup(32,GPIO.OUT)
GPIO.setup(36,GPIO.OUT)
GPIO.setup(40,GPIO.OUT)
PWM=GPIO.PWM(32,60)       #GPIO pin 32 set for Pulse Width
                           Modulation.
                           Second number in parentheses is Hz.
IN1=36                    #GPIO 36=IN1 on motor controller
IN2=40                    #GPIO 40=IN2 on motor controller
print ("Motor On at 100%")
PWM.start(100)            #number in parentheses=duty cycle.
                           Valid entries are >=0 (slowest) and <=0
                           (fastest).
```

```
GPIO.output(IN1,GPIO.HIGH)
GPIO.output(IN2,GPIO.LOW)
time.sleep (30)
PWM.stop( )               #Stop PWM output.
Print ("Motor Off")
GPIO.cleanup( )
```

Additional Embodiment of Automated Apparatus and Method

Figures 20C, 20D:
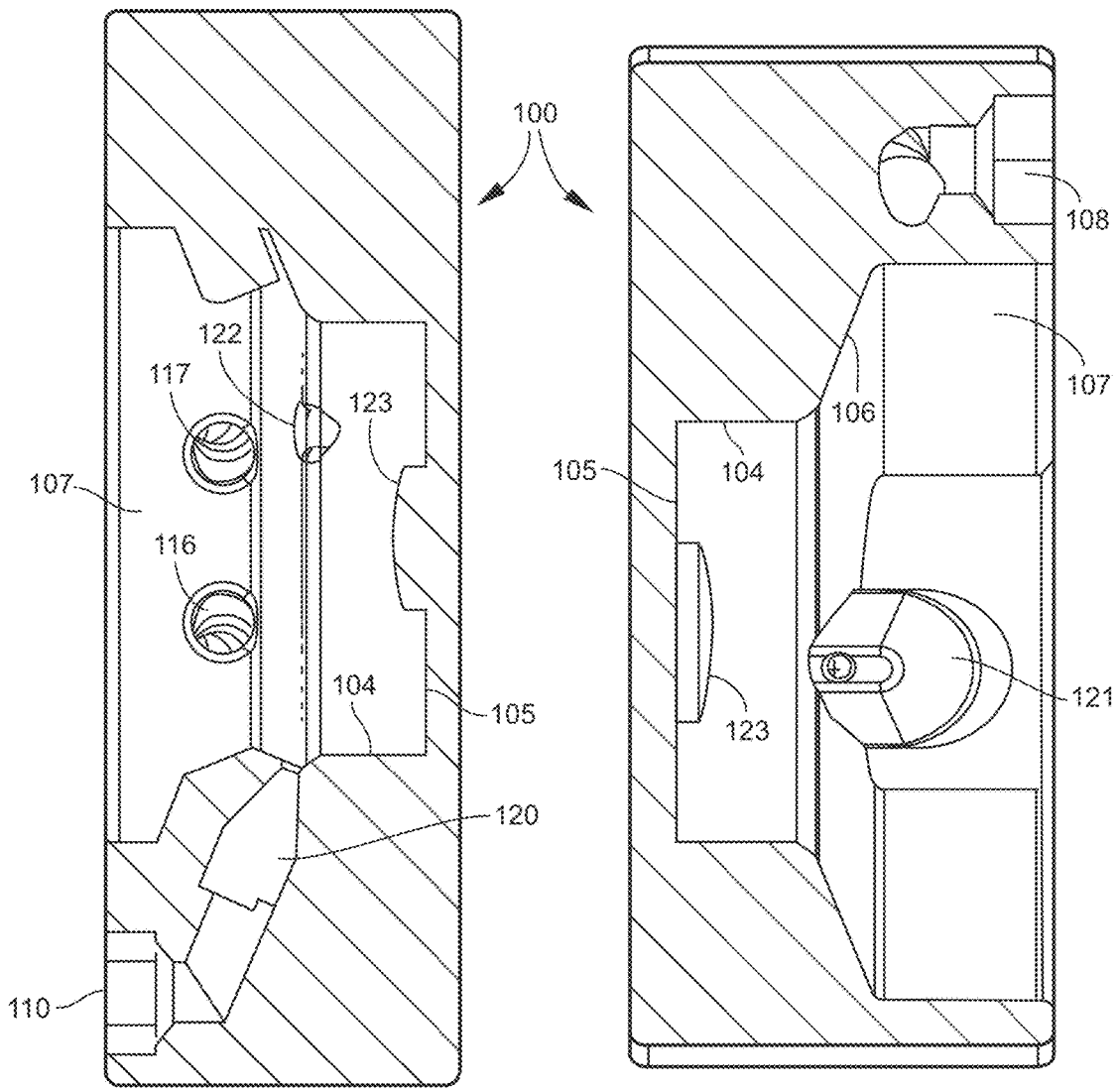
FIG. 20C is a sectional view along the line BB of FIG. 20.
FIG. 20D is a sectional view along the line CC of FIG. 20.

FIGS. 18A, 18B, 18C, 18D and 18E are top, bottom end, right side, left side and top end views, respectively, of an embodiment of a housing 100 for a device for isolating CECs. FIGS. 19A-D are perspective views and FIG. 19E is a bottom view of the housing 100 of FIGS. 18A-E. FIG. 20A is a top view of the housing 100 with lines for sectional views. FIG. 20B is a sectional view along the line AA of FIG. 20. FIG. 20C is a sectional view along the line BB of FIG. 20. FIG. 20D is a sectional view along the line CC of FIG. 20.

Referring to FIGS. 19A-E, an apparatus for isolating corneal endothelial cells (CECs) includes a housing 100 having an exterior wall 101 and an interior wall 102. The interior wall 102 defines a hollow interior 103 of the housing 100. The hollow interior 103 has a central longitudinal axis X. The interior wall 102 of the housing 100 has a lower portion 104 that extends upwardly and generally perpendicular to a circular base 105. The interior wall 102 has a middle portion 106 that angles upwardly away from the lower portion 104 and an upper portion 107 that extends upwardly from the middle portion 106. As shown in FIG. 20B, angle A is the angle between the middle portion 106 and the horizontal and may be in a range of about 10-60 degrees and preferably in a range of about 15-35 degrees.

At least four fluid channels 108, 109, 110, 111 are formed in the housing 100. Fluid channels 108, 109 terminate as openings 116, 117 in the upper portion 107 of the interior wall 102. Fluid channels 110, 111 terminate as jets 120, 121 in the upper portion 107 of the interior wall 102. One jet 120 is located circumferentially approximately opposite the other jet 121. Jets 120, 121 may be conical jets. A drain port 122 is formed at the intersection of the lower and middle portions 104, 106 of the interior wall 102. Drain port 122 connects to fluid channel 112.

Referring to FIG. 20A, a convex projection 123 is centrally located on the circular base 105 and configured to receive an inverted cornea 32 (see FIGS. 8 and 9). The convex projection 123 may have a circular or oval circumference. The jets 120, 121 are offset on opposite sides of the center of the convex projection 123 so that the fluid exhausted from the jets will impart a rotation of the fluid around the center of the convex projection 123 and increase cell detachment from the cornea 32. Jets 120, 121 are preferably angled downwardly so that the fluid exhausted from the jets is aimed at points slightly offset from the center of the cornea to thereby increase cell detachment.

Figure 22:
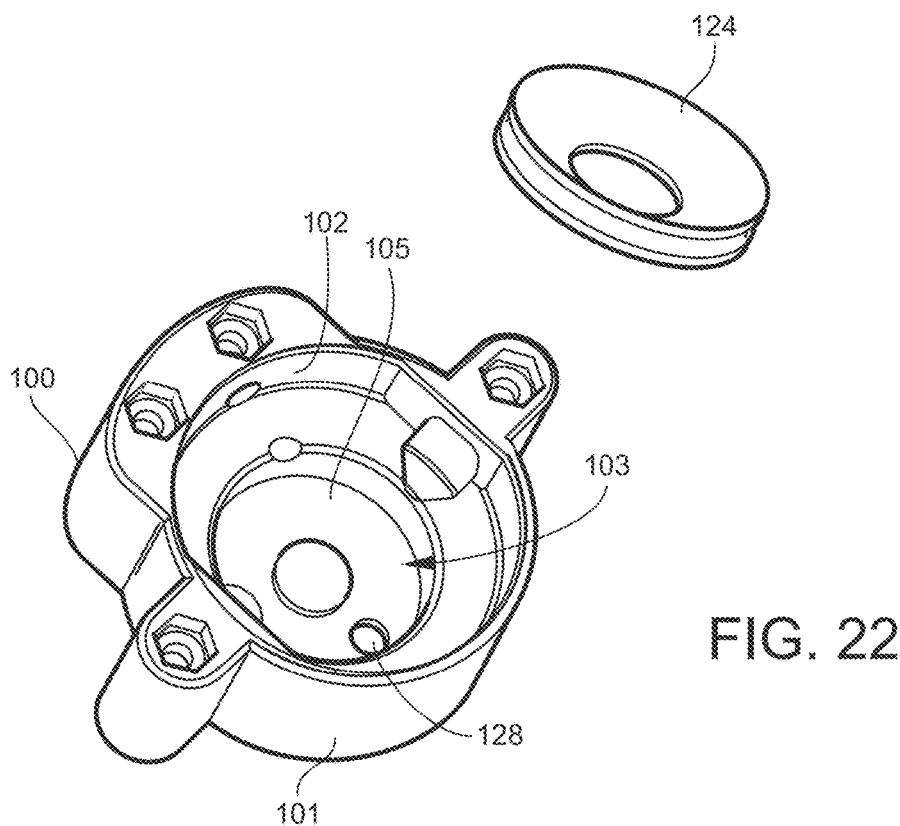
FIG. 22 is an exploded top side perspective view of a device for isolating CECs including the housing of FIGS. 18A-E and the insert of FIGS. 21A-E.

FIGS. 21A, 21B, 21C, 21D and 21E are perspective, top, bottom, horizontal side and vertical side (rotated 90 degrees from FIG. 21D) views of an insert 124 for the housing 100 of FIGS. 18A-E. FIG. 22 is an exploded top side perspective view of a device for isolating CECs including the housing 100 of FIGS. 18A-E and the insert 124 of FIGS. 21A-E.

The outer circumference of circular insert 124 is configured to mate with the lower portion 104 of the interior wall 102. The circular insert 124 may include a circumferential groove 127 formed thereon and an O-ring 44 (FIG. 10) inserted in the groove 127 to seal the circular insert to the lower portion 104 of the interior wall 102. The circular insert 124 has an opening 125 therein in which the convex projection 123 projects when the insert 124 is mated with the lower portion 104 of the interior wall 102. In the illustrated embodiment, the opening 125 is circular in shape. In some embodiments, the opening 125 may have an elliptical shape.

Figure 26:
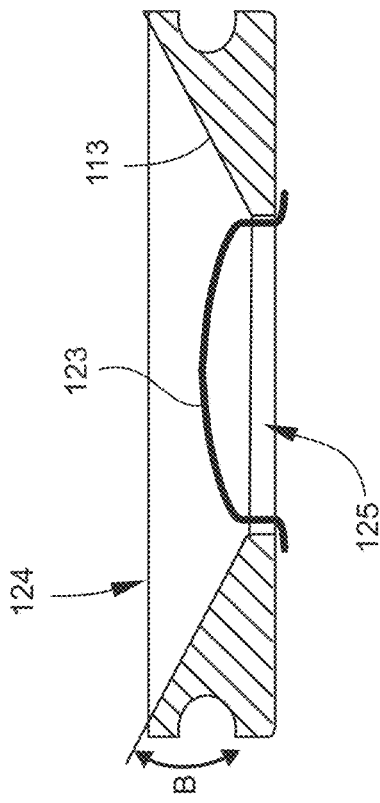
FIG. 26 is schematic sectional view of the insert of FIGS. 21A-E taken along a bisecting central line.

FIG. 26 is sectional view of the insert 124 taken along a bisecting central line. Insert 124 includes a top surface 113 that angles upwardly away from the opening 125 to the circumference of the insert. The angle B between the top surface 124 and the horizontal is preferably between about 25 to 45 degrees and more preferably is about 30 degrees.

Prior to placing circular insert 124 in housing 100, an inverted cornea 32 (see FIGS. 8 and 9, for example) is placed on the convex projection 123. Then, circular insert 124 is placed over and around cornea 32 and convex projection 123. Cornea 32 and a portion of projection 123 extend through circular opening 125 in insert 124. The inverted cornea 32, projection 123 and the circumference of circular opening 125 form a fluid seal. In addition, the circumferential groove 127 of insert 124, O-ring 44 and lower portion 104 of interior wall 102 from a fluid seal. So, interior space 103 above the circular insert 124 is fluidly sealed from the interior space 103 below the circular insert 124.

Preferably, the insert 124 fits in the housing 100 such that the intersection of the sloping top surface 113 of the insert is aligned with, continuous with, or creates a smooth transition with the sloping middle portion 106 of the interior wall 102. When the cornea 32 is placed over the convex projection 123 and the insert 124 is placed over the cornea 32, the cornea 32 covers the projection 123 so that the endothelial layer is the only part of the cornea that is exposed to the upper interior 103 of the housing and the digestive enzymes contained therein. If the projection 123 is too high or if the opening 125 of insert 124 is too wide, then, in addition to the endothelial layer being exposed to the digestive enzymes, the sclera next to the endothelium would also be exposed. Exposing the sclera to the digestive enzymes is undesirable. If the projection 123 is too low or if the opening 125 is too small, then the endothelium at the circumference of the cornea will not be exposed to the digestive enzymes (it would be covered by the insert 124). Coverage of the endothelium in this manner would undesirably inhibit isolation of the covered CECs.

A plurality of the circular inserts 124 may be provided. The openings 125 in inserts 124 may have different diameters. The differing diameters of the openings 125 may be used to accommodate different size corneas, for example, corneas from different species of animals. For a guinea pig cornea, the diameter of opening 125 may be, for example, 7 mm. For a human cornea, the diameter of opening 125 may be, for example, 11.5 mm. The diameter of opening 125 is set to be equal to the diameter of the cornea. The cornea may be slightly stretched to account for minor differences in the diameter of the cornea in the vertical and horizontal direction. Slightly stretching the cornea may be advantageous because it facilitates degradation of the CEC attachment sites by enzymes. The diameter and shape of the convex projection 123 may also be varied to accommodate different size or shaped corneas.

The height of the convex projection 123 may vary with the height of the cornea as measured from the cornea center to the cornea periphery. This adjustment is necessary because corneas from different species cover different percentages of the eye globe. For example, porcine corneas occupy a smaller percentage of the porcine eye globe compared to the percentage that a guinea pig cornea covers a guinea pig eye globe. In other words, the periphery of the guinea pig cornea extends further back toward the eye socket than the periphery of the porcine eye globe.

Figure 24:
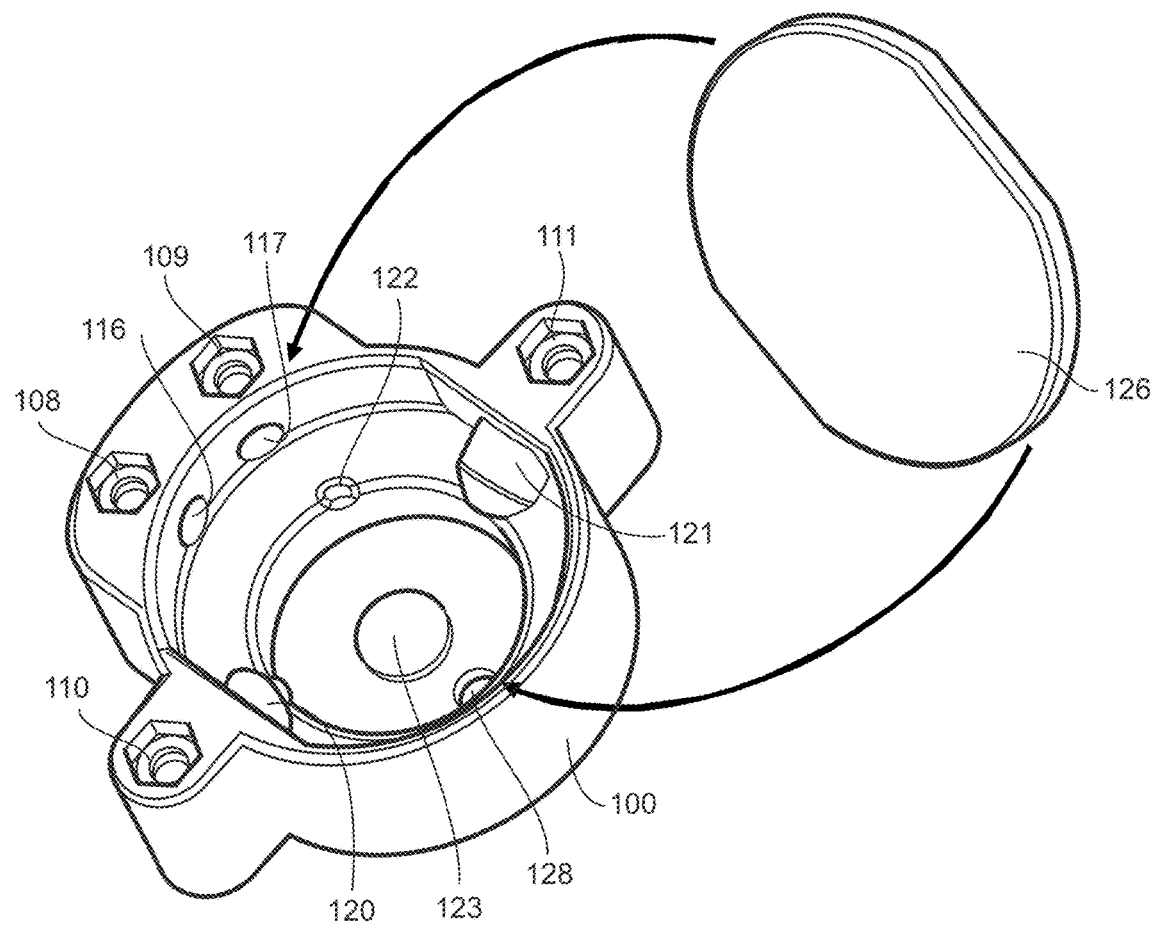
FIG. 24 is an exploded perspective view of the housing showing a cover for closing the housing.

FIG. 24 is a perspective view of the housing 100 and a cover 126 for closing the housing 100. Cover 126 may close the hollow interior 103 of the housing 100 above the fluid channel openings 116, 117 and jets 120, 121 in the upper portion 107 of the interior wall.

Figure 23:
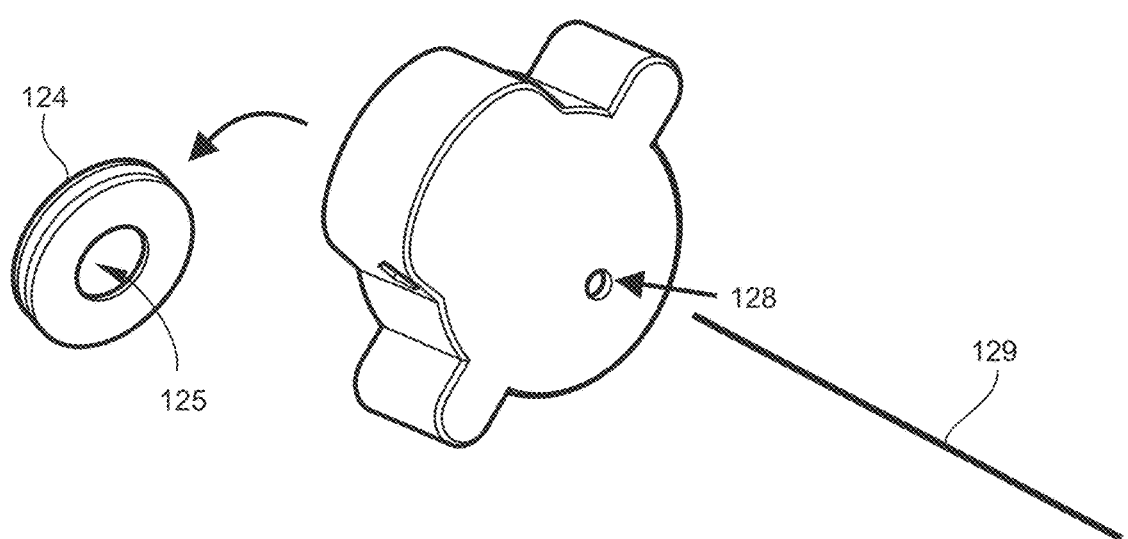
FIG. 23 is an exploded bottom side perspective view of a device for isolating CECs illustrating a method for removing the insert from the housing using a dowel inserted in an opening in the housing.

FIG. 23 is an exploded bottom side perspective view of the housing 100 and insert 124. To remove insert 124 from housing 100, a dowel 129 may be inserted in an opening 128 in the bottom of housing 100.

The housing 100, circular insert 124 and cover 126 may be configured for printing by a 3D printer. The 3D printable design is particularly advantageous in that the same basic design of the isolation device can be utilized for different species, with slight alterations in the diameter /shape of opening 125 and the diameter/shape and height of projection 123. These changes can be made in the computer-assisted drawing (CAD) file that defines each device component before export to a machine capable of 3D printing. Multiple copies of the device can be readily manufactured according to need. The isolation device may be 3D printed using a material such as, for example, polylactic acid. Polylactic acid can be sterilized using low temperature processes such as alcohol immersion or ethylene oxide exposure. If high temperature sterilization methods such as autoclaving are desired, a 3D printer capable of printing with metallic material may be used to manufacture the isolation device.

Figure 25:
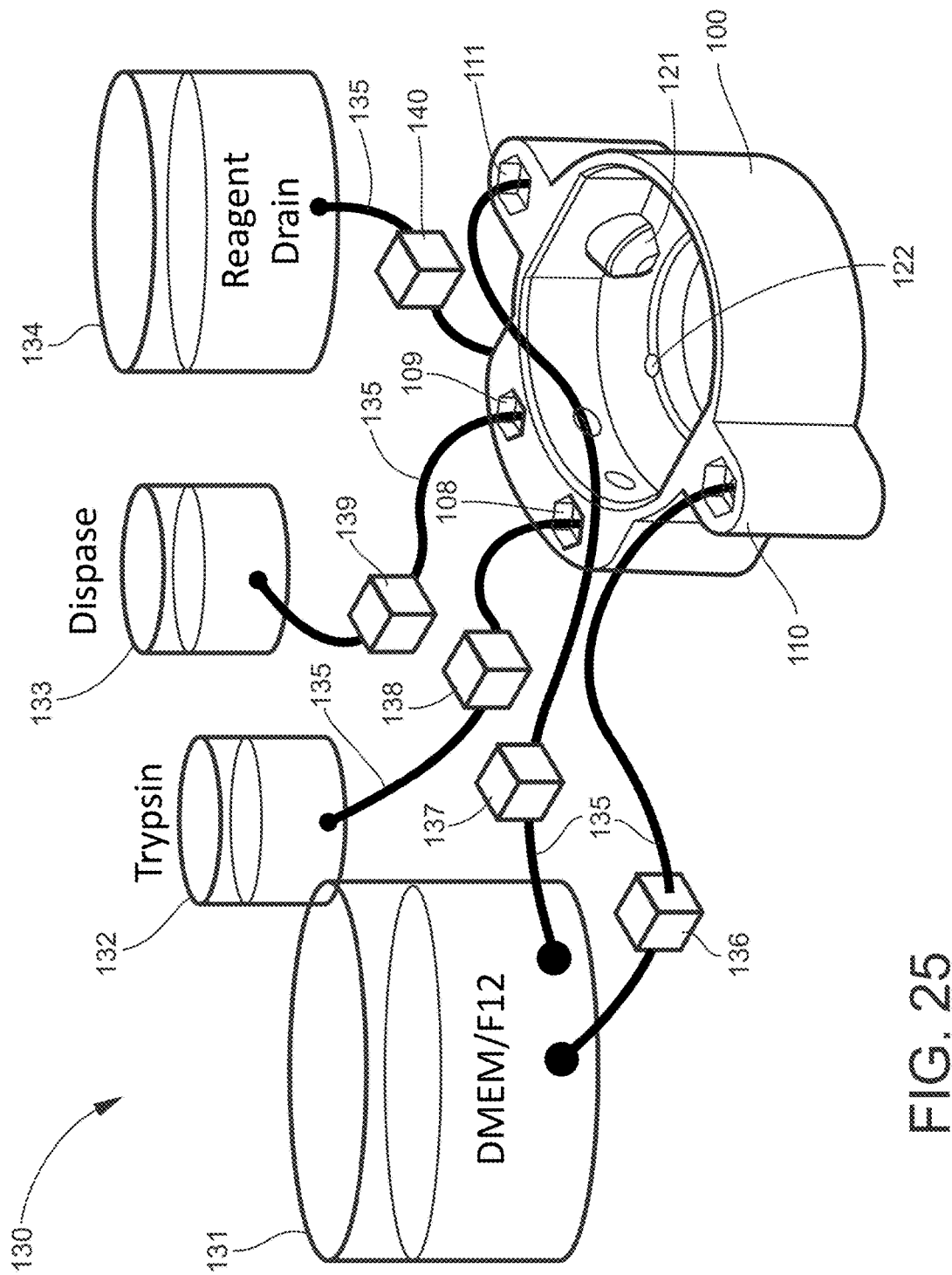
FIG. 25 is a schematic of an automated CEC isolation system.
Figure 27:
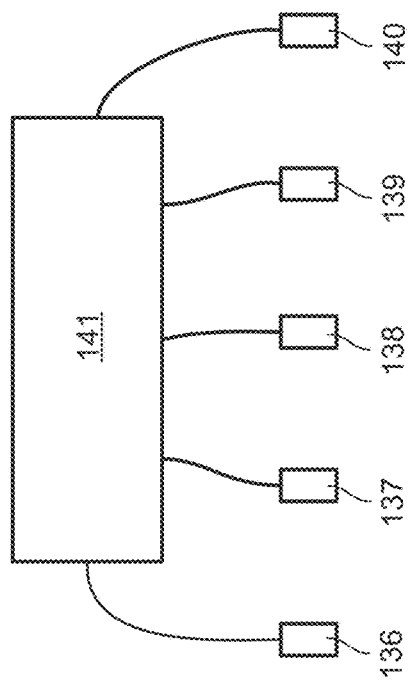
FIG. 27 is a schematic of a microprocessor controller connected to the pump/motors of FIG. 25.3

FIG. 25 is a schematic of an automated CEC isolation system 130. Four fluid containers or vessels 131, 132, 133, 134 are connected via tubing 135 to five fluid channels 108, 109, 110, 111, 112 in housing 100 (See FIG. 19C for fluid channel 112). Tubing 135 may be, for example, plastic tubing. Fluids are moved from containers 131, 132, 133, 134 to housing 100 or vice versa by pump/motor devices 136, 137, 138, 139, 140. As shown in FIG. 27, a microprocessor 141 is electrically connected to the pump/motor devices 136, 137, 138, 139, 140 to supply power and control.

Container 131 contains isotonic solution DMEM/F 12. Container 132 contains trypsin. Container 133 contains dispase. Container 134 holds the solution with CECs therein that is flushed from housing 100. Pump/motor 136 supplies jet nozzle 120 with isotonic solution (DMEM/F12) and pump/motor 137 supplies jet nozzle 121 with isotonic solution (DMEM/F12). Jet nozzles 120, 121 expel the solution at high pressure onto the endothelial surface of the cornea 32 to facilitate cell detachment. Pump/motor 138 transfers 5 mLs trypsin, for example, to the housing interior 103 above the circular insert 124 at the beginning of the isolation process. The corneal endothelial tissue is digested for 7 minutes, for example, in the trypsin. After trypsin digestion, pump/motor 138 transfers 10 mL dispase, for example, to the housing interior. The tissue is digested for 20 minutes in dispase, for example. After dispase digestion, pump/motors 136, 137 expel isotonic solution at high pressure onto the tissue surface for 15 seconds, for example. Dislodged corneal endothelium cells 34 are now suspended in solution. Pump/motor 140 transfers solution from the housing chamber to sterile cylindrical vessel 134. The bottom surface of the receiving vessel 134 may be fabricated using polycarbonate (PC) plastic. PC is known to be compatible with cellular attachment and growth.

A second 20 minute digestion in dispase may then be implemented, followed by another high pressure wash generated by pump/motors 136, 137. All solutions are transferred to the receiving vessel 134 by pump/motor 140. The following day, isolated cells 34 will be attached to the PC surface. The solution within the vessel 134 can be manually aspirated and replaced with fresh growth medium. This strategy allows the newly isolated endothelial cells 34 to remain on the PC surface until the population grows to 100% confluency.

Setup

In a sterile hood, the operator connects the fluid containers 131, 132, 133, 134 to fluid channels 108, 109, 110, 111, 112 on the housing 100. The operator adds DMEM/F12, trypsin and dispase to the corresponding fluid containers, 131, 132 and 133, respectively. The operator primes the pump/motors 136, 137, 138, 139. The operator aspirates the housing chamber. The operator dissects out the cornea 32 and secures the corneal tissue in the housing chamber. The operator adds 5 mL DMEM/F12 to the chamber. The operator transfers the assembly to a 37° C. incubator. The operator connects the microprocessor. The operator initiates the Python script that controls the isolation device electronics and motors during processing.

Exemplary Code Summary

The controller script defines the automated process as follows:

1) Assembly Warm-Up

Wait 20 minutes at 37° C. for solutions, component parts, and corneal tissue to reach temperature. Transfer DMEM/F12 from housing chamber to vessel 134 using pump/motor 140. (This step removes DMEM /F12 that was placed in the housing chamber by the operator to keep tissue hydrated during warm up of assembly.)

2) Trypsin Digestion

Using pump/motor 138, add 5 mL trypsin to housing chamber. Wait 7 minutes.

3) First Dispase Digestion

Using pump/motor 139, add 10 mL dispase to chamber. Allow tissue digestion for 20 minutes. Run pump/motors 136, 137 to transfer DMEM/F12 to jets 120, 121 for 15 seconds. Using pump/motor 140, drain housing chamber to vessel 134. Using pump/motors 136, 137, add 10 mL DMEM/F12 to isolation chamber. Run pump/motors 136, 137 for 15 seconds. Using pump/motor 140, drain the housing chamber to vessel 134.

4) Second Dispase Digestion

Using pump/motor 139, add 10 mL dispase to chamber. Allow tissue digestion for 20 minutes. Run pump/motors 136, 137 for 15 seconds. Using pump/motor 140, drain the housing chamber to vessel 134. Using pump/motor 139, add 10 mL dispase to chamber. Run pump/motors 136, 137 for 15 seconds. Using pump/motor 140, drain the housing chamber to vessel 134. The following day, observe yield and cell morphology of the isolate. Acquire micrographs for documentation. Feed culture every two-to-three days.

Embodiments of the invention have been described to explain the nature of the invention. Those skilled in the art may make changes in the details, materials, steps and arrangement of the described embodiments within the principle and scope of the invention, as expressed in the appended claims.

What is claimed is:

1. An apparatus for isolating corneal endothelial cells (CECs), comprising:
   a housing having an exterior wall and an interior wall that defines a hollow interior of the housing, the hollow interior having a central longitudinal axis;

the interior wall of the housing having a lower portion that extends upwardly and generally perpendicular to a circular base, a middle portion that angles upwardly away from the lower portion and an upper portion that extends upwardly from the middle portion;

at least four fluid channels formed in the housing with two of the channels terminating in respective openings in the upper portion of the interior wall and two of the channels terminating in respective jets in the upper portion of the interior wall wherein one jet is located circumferentially approximately opposite the other jet;

a drain port formed near an intersection of the middle and lower portions of the interior wall and leading to a fifth fluid channel formed in the housing;

a convex projection centrally located on the circular base and configured to receive an inverted cornea; and a circular insert having an outer circumference configured to mate with the lower portion of the interior wall, the circular insert having an opening therein in which the convex projection projects when the insert is mated with the lower portion of the interior wall.

2. The apparatus of claim 1, further comprising a cover that closes the hollow interior of the housing above the fluid channel openings and jets in the upper portion of the interior wall.

3. The apparatus of claim 1, further comprising a circumferential groove formed in the circular insert and an O-ring inserted in the groove to seal the circular insert to the lower portion of the interior wall of the housing.

4. The apparatus of claim 1, further comprising an opening formed in the circular base.

5. The apparatus of claim 1, wherein an angle between the middle portion of the interior wall and a horizontal is in a range of about 10 degrees to 60 degrees.

6. The apparatus of claim 1, wherein the circular insert includes a top surface that angles upwardly from the opening in the circular insert to a circumference of the circular insert.

7. The apparatus of claim 6, wherein an angle between the top surface of the circular insert and a horizontal is in a range of about 25 degrees to about 45 degrees.

8. The apparatus of claim 1, wherein the CECs are mammalian CECs.

9. A method for isolating corneal endothelial cells (CECs), comprising:
providing the apparatus of claim 1 and a cornea;
placing the cornea with its endothelial side up over the convex projection; and
mating the circular insert with the housing such that the convex projection extends into the opening of the insert and an endothelial layer of the cornea contacts an entire circumference of the opening of the insert wherein only the endothelial layer of the cornea is exposed to the hollow interior above the circular insert.

10. The method of claim 9, further comprising adding trypsin to the interior of the housing.

11. The method of claim 10, further comprising digesting proteins in a Descemet's Membrane of the cornea by adding dispase to the interior of the housing.

12. The method of claim 11, further comprising adding an isotonic solution to the interior of the housing using jets aimed at the cornea.

13. The method of claim 11, further comprising removing fluids from the interior of the housing via the drain port and the fifth fluid channel.

14. An assembly, comprising:
the apparatus of claim 1;
a first fluid container connected to the respective jets in the housing via first and second tubing;
first and second pump/motor devices inserted in the first and second tubing for moving fluid from the first fluid container to the jets;
second and third fluid containers connected to the respective openings in the upper portion of the interior wall via third and fourth tubing;
third and fourth pump/motor devices inserted in the third and fourth tubing for moving fluid from the second and third containers to the respective openings in the upper portion of the interior wall;
a fourth fluid container connected to the drain port and the fifth fluid channel in the housing via fifth tubing;
a fifth pump/motor device inserted in the fifth tubing for moving fluid that contains CECs from the housing to the fourth fluid container; and
a microprocessor controller connected to each of the five pump/motor devices.

15. The assembly of claim 14, further comprising a cover that closes the hollow interior of the housing above the fluid channel openings and jets in the upper portion of the interior wall.

16. The assembly of claim 15, further comprising an isotonic solution in the first fluid container.

17. The assembly of claim 16, further comprising trypsin in the second fluid container.

18. The assembly of claim 17, further comprising dispase in the third fluid container.

19. The assembly of claim 18, further comprising the fluid that contains CECs in the fourth fluid container.

20. The apparatus of claim 19, wherein a bottom surface of the fourth fluid container includes polycarbonate (PC) plastic.

* * * * *